(12) United States Patent
Trieselmann et al.

(10) Patent No.: US 7,977,334 B2
(45) Date of Patent: Jul. 12, 2011

(54) BETA-AGONISTS, METHODS FOR THE PREPARATION THEREOF AND THEIR USE AS PHARMACEUTICAL COMPOSITIONS

(75) Inventors: Thomas Trieselmann, Warthausen (DE); Bradford S. Hamilton, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 280 days.

(21) Appl. No.: 12/113,780

(22) Filed: May 1, 2008

(65) Prior Publication Data

US 2008/0234278 A1 Sep. 25, 2008

Related U.S. Application Data

(63) Continuation of application No. 11/118,295, filed on Apr. 29, 2005, now abandoned.

(30) Foreign Application Priority Data

Apr. 30, 2004 (DE) .................. 10 2004 021 779

(51) Int. Cl.
*A61K 31/50* (2006.01)
*C07D 249/04* (2006.01)

(52) U.S. Cl. ........ 514/248; 514/398; 514/387; 548/255; 548/302.7; 548/335.5; 544/235

(58) Field of Classification Search .............. 548/255, 548/302.7, 335.524; 514/248, 398, 387; 544/235

See application file for complete search history.

(56) References Cited

U.S. PATENT DOCUMENTS

| | | | |
|---|---|---|---|
| 2,943,090 A | 6/1960 | Semb et al. | |
| 3,092,636 A | 6/1963 | Heinzelman et al. | |
| 4,154,829 A | 5/1979 | Mentrup et al. | |
| 4,215,119 A | 7/1980 | Mentrup et al. | |
| 4,363,814 A | 12/1982 | Mentrup et al. | |
| 4,478,849 A | 10/1984 | Ainsworth | |
| 4,647,563 A | 3/1987 | Schromm et al. | |
| 6,667,342 B1 | 12/2003 | Clarke et al. | |
| 7,214,698 B2 * | 5/2007 | Trieselmann et al. | 514/399 |
| 2003/0191174 A1 * | 10/2003 | Ikuta et al. | 514/415 |
| 2004/0127733 A1 | 7/2004 | Trieselmann et al. | |
| 2005/0020602 A1 | 1/2005 | Miyoshi et al. | |
| 2005/0245526 A1 | 11/2005 | Trieselmann et al. | |
| 2007/0105906 A1 | 5/2007 | Walter et al. | |
| 2007/0112033 A1 | 5/2007 | Trieselmann et al. | |
| 2008/0103138 A1 | 5/2008 | Trieselmann et al. | |
| 2008/0269281 A1 | 10/2008 | Trieselmann et al. | |
| 2008/0300290 A1 | 12/2008 | Walter et al. | |

FOREIGN PATENT DOCUMENTS

| | | |
|---|---|---|
| CA | 2504213 A1 | 5/2004 |
| CA | 2564980 A1 | 11/2005 |
| DE | 2115926 | 10/1972 |
| EP | 0008653 | 3/1980 |
| EP | 0177245 A2 | 4/1986 |
| EP | 0659737 | 6/1995 |
| EP | 1277736 | 1/2003 |
| EP | 1447400 | 8/2004 |
| GB | 1200886 | 8/1970 |
| GB | 2356197 | 5/2001 |
| WO | 9529159 A1 | 11/1995 |
| WO | 9721665 A1 | 6/1997 |
| WO | 0040560 | 7/2000 |
| WO | 0162705 | 8/2001 |
| WO | 0183452 | 11/2001 |
| WO | 0200622 | 1/2002 |
| WO | 0206281 | 1/2002 |
| WO | 03072572 | 9/2003 |
| WO | 2004-39784 | 5/2004 |
| WO | 2005108373 A1 | 11/2005 |

OTHER PUBLICATIONS

Arch; B3-Andrenoceptor agonists: potential, pitfalls and progress; European Journal of Pharmacology; 2002; vol. 440; pp. 99-107.

Clifton et al.; Arylethanolamines derived from salicylamide with .alpha.- and .beta.-adrenoceptor blocking activities. Preparation of labetalol, its enantiomers and related salicylamides; Journal of Medicinal Chemistry; 1982; vol. 25; No. 6; pp. 670-679.

Kawashima Kazu; Publication No. 08165276; Publication Date Jun. 25, 1996; 2-akylamino-1-phenylethanol derivative; Patent Abstracts of Japan; vol. 1996; No. 10.

Harada et al.; Discovery of a Novel and Potent Human and Rat B3-Adrenergic Receptor Agonist, [3-[(2R)-[[(2R)-(3Chlorophenyl)-2-hydroxyethyl]amino]propyl]-1H-indol-7-yloxy]acetic Acid; Chemical & Pharmaceutical Bulletin; Feb. 2005; vol. 53; No. 2; pp. 184-198.

Moffett; New compounds with possible pharmacological activity; Journal of Chemical and Engineering Data; 1980; vol. 25; No. 2; pp. 176-183.

(Continued)

*Primary Examiner* — Rei-tsang Shiao
(74) *Attorney, Agent, or Firm* — Michael P. Morris; Edward S. Lazer

(57) ABSTRACT

The present invention relates to new beta-agonists of general formula (I)

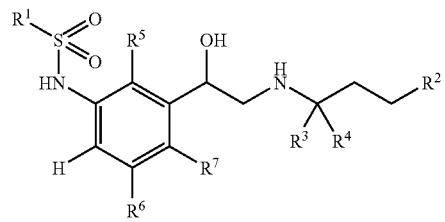

wherein the groups $R^1$ to $R^7$ have the meanings given in the claims and specification, the tautomers, the enantiomers, the diastereomers, the mixtures thereof, the prodrugs thereof and the salts thereof, particularly the physiologically acceptable salts thereof with inorganic or organic acids or bases, processes for preparing these compounds and their use as pharmaceutical compositions.

18 Claims, No Drawings

OTHER PUBLICATIONS

Thompson et al.; Protein Conformational Misfolding and Amyloid Formation: Characteristics of a New Class of Disorders that Include Alzheimer's and Prion Diseases; Current Medicinal Chemistry; 2002; vol. 9; pp. 1751-1762.

International Search Report, Form PCT/ISA/210, for corresponding PCT/EP2006/067868; mailed on Jan. 9, 2007.

International Search Report, Form PCT/ISA/210, for corresponding PCT/EP2006/067874; mailed on Jan. 5, 2007.

International Search Report, Form PCT/ISA/210, for corresponding PCT/EP2006/067875; mailed on Mar. 30, 2007.

International Search Report for PCT/EP2005/004385 mailed on Sep. 15, 2005.

* cited by examiner

BETA-AGONISTS, METHODS FOR THE PREPARATION THEREOF AND THEIR USE AS PHARMACEUTICAL COMPOSITIONS

CROSS-REFERENCE TO RELATED APPLICATIONS

This application is a continuation of U.S. application Ser. No. 11/118,295, filed on Apr. 29, 2005, which claims the benefit of DE 102004021779, filed Apr. 30, 2004.

The present invention relates to new beta-agonists of general formula (I)

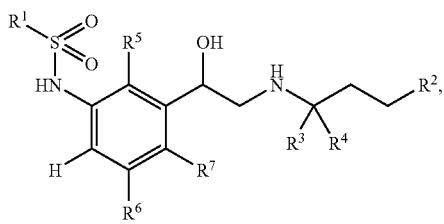

wherein the groups $R^1$ to $R^7$ have the meanings given below in the specification, the tautomers, the enantiomers, the diastereomers, the mixtures thereof, the prodrugs thereof and the salts thereof, particularly the physiologically acceptable salts thereof with inorganic or organic acids or bases, processes for preparing these compounds and their use as pharmaceutical compositions.

BACKGROUND OF THE INVENTION

The treatment of type II diabetes and obesity is based primarily on reducing calorie intake and increasing physical activity. These methods are rarely successful in the longer term.

It is known that beta-3 receptor agonists have a significant effect on lipolysis, thermogenesis and the serum glucose level in animal models of type II diabetes (Arch JR. beta(3)-Adrenoceptor agonists: potential, pitfalls and progress, Eur J Pharmacol. 2002 Apr. 12; 440(2-3):99-107).

Compounds which are structurally similar to the compounds according to the invention and their broncholytic, spasmolytic and antiallergic activities were disclosed in DE 2833140, for example.

The aim of the present invention is to provide selective beta-3 agonists which can be used to prepare pharmaceutical compositions for the treatment of obesity and type II diabetes.

DETAILED DESCRIPTION OF THE INVENTION

Surprisingly it has been found that compounds of general formula (I) wherein the groups $R^1$ to $R^7$ are defined as hereinafter are effective as selective beta-3 agonists. Thus, the compounds according to the invention may be used to treat diseases connected with the stimulation of beta-3-receptors.

The present invention therefore relates to compounds of general formula (I)

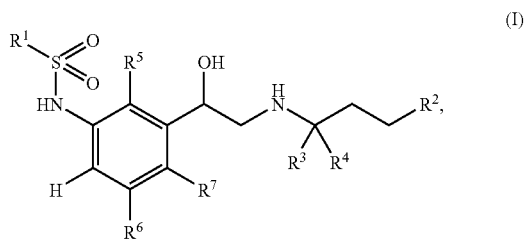

wherein
$R^1$ denotes an optionally substituted aryl or heteroaryl group,
$R^2$ denotes an optionally substituted heteroaryl or heterocyclyl group, while $R^2$ contains at least one nitrogen atom,
$R^3$ and $R^4$ independently of one another denote a hydrogen atom or an optionally substituted group selected from the group comprising $C_1$-$C_5$-alkyl, $C_3$-$C_6$-cyclo-alkyl, heterocyclyl, aryl and heteroaryl or
$R^3$ and $R^4$ together represent a 2- to 7-membered alkylene bridge,
$R^5$, $R^6$ and $R^7$ independently of one another denote a hydrogen atom or a group selected from the group comprising optionally substituted $C_1$-$C_{10}$-alkyl, alkenyl, alkynyl, $C_6$-$C_{10}$-aryl, heterocyclyl, $C_3$-$C_8$-cycloalkyl, —$NR^8$—($C_1$-$C_5$-alkyl), —$NR^8$-aryl, halogen, cyano, —$NR^8CO$—($C_1$-$C_5$-alkyl), —$NR^8CO$-aryl, —$NR^8SO_2$—($C_1$-$C_5$-alkyl), —$NR^8SO_2$-aryl, —$CO_2R^8$, —$SO_2R^8$, —$CONHR^8$, —$SO_2NHR^8$ and —$OR^8$, while the above-mentioned alkyl groups may be substituted in each case, and
$R^8$ denotes a hydrogen atom or a $C_1$-$C_5$-alkyl group,
optionally in the form of the tautomers, racemates, enantiomers, diastereomers, solvates and hydrates thereof and the mixtures thereof, as well as optionally the prodrugs, double prodrugs and salts thereof, particularly the physiologically acceptable salts thereof with inorganic or organic acids or bases.

Preferred are compounds of general formula (I), wherein
$R^2$ to $R^7$ are as hereinbefore defined and
$R^1$ denotes an optionally substituted phenyl group.

Another preferred sub-group relates to the compounds of general formula (I), wherein
$R^1$ and $R^3$ to $R^7$ are as hereinbefore defined,
$R^2$ denotes a group selected from among the optionally substituted groups of formulae:

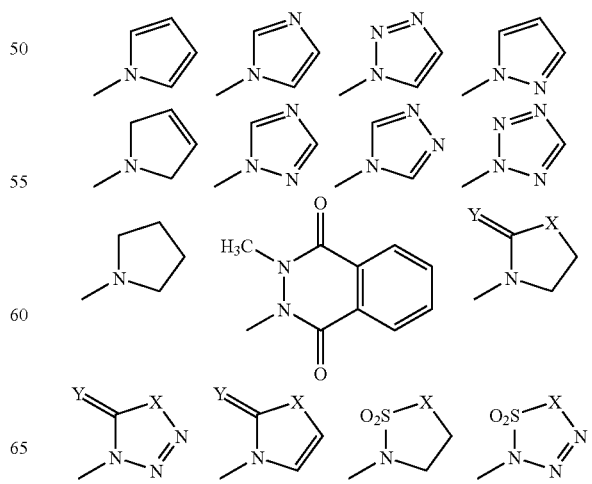

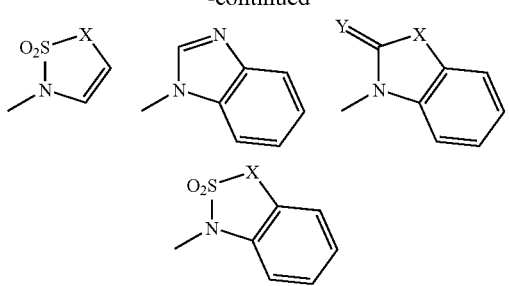

while the above-mentioned groups may be substituted in each case by one or more groups $R^{10}$ and $R^{10}$ denotes OH, $NO_2$, CN, —$OCHF_2$, —$OCF_3$, —$NH_2$, —NH-alkyl, —N(-alkyl)-alkyl, —NH-aryl, —N(-alkyl)-aryl, —NHCO-alkyl, —$NHCO_2$-alkyl, —NHCO-aryl, —N(-alkyl)-CO-alkyl, —N(-alkyl)-CO-aryl, —$NHSO_2$-alkyl, —$NHSO_2$-aryl, —N(-alkyl)-$SO_2$-alkyl, —N(-alkyl)-$SO_2$-aryl, —$CO_2$-alkyl, —$SO_2$-alkyl, —$SO_2$-aryl, —CONH-alkyl, —CONH-aryl, —CON(-alkyl)-alkyl, —CON(-alkyl)-aryl, —$SO_2$NH-alkyl, —$SO_2$NH-aryl, —$SO_2$N(-alkyl)-alkyl, —$SO_2$N(-alkyl)-aryl, —O-alkyl, —O-aryl, —S-alkyl, —S-aryl, halogen, $C_1$-$C_{10}$-alkyl, —O—($C_1$-$C_3$-alkyl), —COOH, —$CONH_2$, —CON(-alkyl)-$SO_2$-alkyl, —$CONHSO_2$-alkyl, —CONHOH, 2,5-dihydro-5-oxo-4H-1,2,4-oxadiazol-3-yl, 2,5-dihydro-5-oxo-4H-1,2,4-thiadiazol-3-yl, 2,5-dihydro-2-oxo-3H-1,2,4,5-oxathiadiazol-4-yl, 1-acetyl-2-amino-propen-1-yl, tetrazolyl, heterocyclyl, aryl or heteroaryl, and wherein X denotes an oxygen atom or a —$NR^9$— group and Y denotes an oxygen or sulphur atom, and $R^9$ denotes a hydrogen atom or a group selected from the group comprising $C_1$-$C_{10}$-alkyl, $C_3$-$C_8$-cycloalkyl, heterocyclyl, aryl or heteroaryl, while the groups mentioned for $R^9$ hereinbefore may each case be substituted by one of the groups given for $R^{10}$.

Particularly preferred are compounds of general formula (I), wherein $R^1$ and $R^2$ as well as $R^5$ to $R^7$ are as hereinbefore defined, and $R^3$ and $R^4$ independently of one another denote a hydrogen atom or a methyl or ethyl group or $R^3$ and $R^4$ together represent a 2- to 5-membered alkylene bridge.

Particularly preferred are compounds of general formula (I), wherein $R^1$ to $R^4$ are as hereinbefore defined, and $R^5$, $R^6$ and $R^7$ independently of one another represent hydrogen, optionally substituted $C_1$-$C_{10}$-alkyl, halogen, CN, —$NR^8$CO—($C_1$-$C_5$-alkyl), —$NR^{83}SO_2$—($C_1$-$C_5$-alkyl), —$CO_2R^8$, —$SO_2R^8$, —$CONHR^8$, —$SO_2NHR^8$ or —$OR^8$ and $R^8$ denotes a hydrogen atom or a $C_1$-$C_5$-alkyl group.

Also preferred are compounds of general formula (I), wherein $R^1$ denotes a phenyl group optionally substituted by a halogen atom or a cyano or nitro group, $R^2$ denotes a group selected from among the optionally substituted groups of formulae:

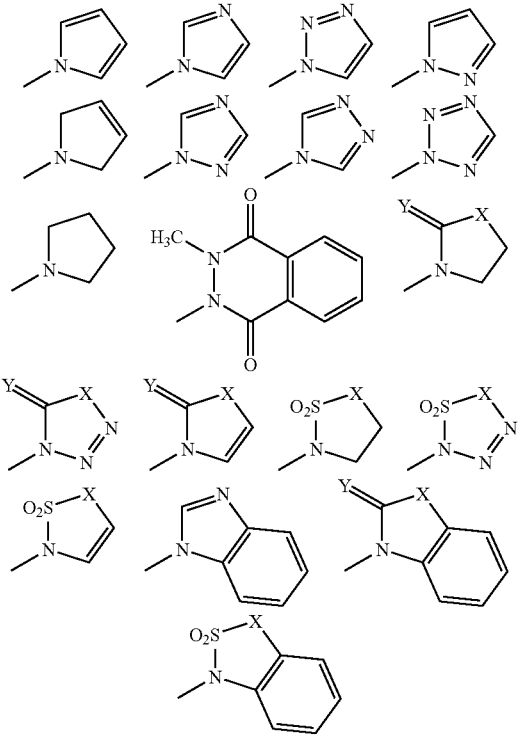

while the above-mentioned groups may each be substituted by one or more groups $R^{10}$ and $R^{10}$ denotes OH, $NO_2$, CN, —$OCHF_2$, —$OCF_3$, —$NH_2$, —NH-alkyl, —N(-alkyl)-alkyl, —NH-aryl, —N(-alkyl)-aryl, —NHCO-alkyl, —$NHCO_2$-alkyl, —NHCO-aryl, —N(-alkyl)CO-alkyl, —N(-alkyl)-CO-aryl, —$NHSO_2$-alkyl, —$NHSO_2$-aryl, —N(-alkyl)-$SO_2$-alkyl, —N(-alkyl)-$SO_2$-aryl, —$CO_2$-alkyl, —$SO_2$-alkyl, —$SO_2$-aryl, —CONH-alkyl, —CONH-aryl, —CON(alkyl)-alkyl, —CON(-alkyl)-aryl, —$SO_2$NH-alkyl, —$SO_2$NH-aryl, —$SO_2$N(-alkyl)-alkyl, —$SO_2$N(-alkyl)-aryl, —O-aryl, —S-alkyl, —S-aryl, halogen, $C_1$-$C_{10}$-alkyl, —O—($C_1$-$C_3$-alkyl), —COOH, —$CONH_2$, —CON(-alkyl)-$SO_2$-alkyl, —$CONHSO_2$-alkyl, —CONHOH, 2,5-dihydro-5-oxo-4H-1,2,4-oxadiazol-3-yl, 2,5-dihydro-5-oxo-4H-1,2,4-thiadiazol-3-yl, 2,5-dihydro-2-oxo-3H-1,2,4,5-oxathiadiazol-4-yl, 1-acetyl-2-amino-propen-1-yl, tetrazolyl, heterocyclyl, aryl or heteroaryl, and wherein X denotes an oxygen atom or a —$NR^9$— group and Y denotes an oxygen or sulphur atom, $R^3$ and $R^4$ independently of one another each denote a methyl or ethyl group or $R^3$ and $R^4$ together represent an ethylene bridge, $R^5$, $R^6$ and $R^7$ independently of one another each denote a hydrogen, fluorine or chlorine atom or a cyano, methoxy, methanesulphonylamino, methanesulphonyl, difluoromethoxy, trifluoromethoxy, difluoromethyl or trifluoromethyl group and $R^9$ denotes a hydrogen atom or an optionally substituted aryl or optionally substituted heteroaryl group.

Particularly preferred are compounds of general formula (I), wherein
$R^1$ denotes a phenyl group optionally substituted by a fluorine, chlorine, bromine or iodine atom or a cyano or nitro group,
$R^2$ denotes a group selected from among the groups of formulae (i)-(vi):

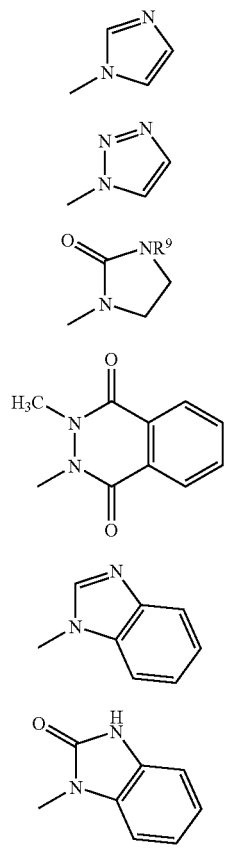

where $R^9$ denotes a phenyl or pyridyl group optionally substituted by a fluorine atom or by an amino, nitro, hydroxy or methoxy group and the above-mentioned groups (i) to (vi) may each be substituted by one or two groups $R^{10}$ and
$R^{10}$ denotes OH, $NO_2$, CN, —$OCHF_2$, —$OCF_3$, —$NH_2$, —NH-alkyl, —N(alkyl)-alkyl, —NH-aryl, —N(alkyl)-aryl, —NHCO-alkyl, —$NHCO_2$-alkyl, —NHCO-aryl, —N(-alkyl)-CO-alkyl, —N(-alkyl)-CO-aryl, —$NHSO_2$-alkyl, —$NHSO_2$-aryl, —N(-alkyl)-$SO_2$-alkyl,
—N(-alkyl)-$SO_2$-aryl, —$CO_2$-alkyl, —$SO_2$-alkyl, —$SO_2$-aryl, —CONH-alkyl, —CONH-aryl, —CON(alkyl)-alkyl, —CON(-alkyl)-aryl, —$SO_2$NH-alkyl, —$SO_2$NH-aryl, —$SO_2$N(-alkyl)-alkyl, —$SO_2$N(-alkyl)-aryl, —O-aryl, —S-alkyl, —S-aryl, halogen, $C_1$-$C_{10}$-alkyl, —O—($C_1$-$C_3$-alkyl), —COOH, —$CONH_2$, —CON(-alkyl)-$SO_2$-alkyl, —$CONHSO_2$-alkyl, —CONHOH, 2,5-dihydro-5-oxo-4H-1,2,4-oxadiazol-3-yl, 2,5-dihydro-5-oxo-4H-1,2,4-thiadiazol-3-yl, 2,5-dihydro-2-oxo-3H-1,2,4,5-oxathiadiazol-4-yl, 1-acetyl-2-amino-propen-1-yl, tetrazolyl, heterocyclyl, aryl or heteroaryl, $R^3$ and $R^4$ independently of one another denote a methyl or ethyl group or
$R^3$ and $R^4$ together represent an ethylene bridge and
$R^5$, $R^6$ and $R^7$ independently of one another denote a hydrogen, fluorine or chlorine atom or a cyano, methoxy, methanesulphonylamino, methanesulphonyl, difluoromethoxy, trifluoromethoxy, difluoromethyl or trifluoromethyl group.
Particularly preferred are compounds of general formula (I), wherein
$R^1$ denotes a phenyl group optionally substituted by a fluorine, chlorine, bromine or iodine atom or a cyano or nitro group,
$R^2$ denotes a group selected from among the groups of formulae (i)-(vi):

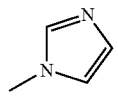

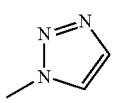

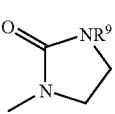

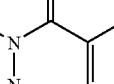

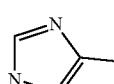

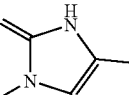

where $R^9$ denotes a phenyl or pyridyl group optionally substituted by a fluorine atom or by an amino, nitro, hydroxy or methoxy group,
and the above-mentioned groups (i) to (vi) may each be substituted by one or two groups $R^{10}$ and
$R^{10}$ denotes OH, —$NO_2$, —CN, —$NH_2$, —I, —$N(CH_3)_2$, —$NHCO_2CH_3$, —$NHSO_2CH_3$, $C_1$-$C_3$-alkyl, —$SO_2N(CH_3)_2$, —$CO_2H$, benzyloxycarbonyl, ethoxycarbonyl, methoxycarbonyl, —CONHOH, tetrazol-5-yl, pyridinyl, methoxy-pyridinyl, phenyl optionally substituted by hydroxy, fluorine, methoxy, amino, nitro, dimethylamino, methylcarbonylamino, methylsulphonylamino, dimethylamino-sulphonylamino, carboxy, ethoxycarbonyl, benzyloxycarbonyl, hydroxyaminocarbonyl or tetrazol-5-yl, or thiophenyl, 5-methyl-thiophen-2-yl, 3,5-dimethyl-isoxazol-4-yl or 1-acetyl-2-amino-propenyl, $R^3$ and $R^4$ in each case denote a methyl or ethyl group or
$R^3$ and $R^4$ together represent an ethylene bridge and
$R^5$, $R^6$ and $R^7$ in each case denote a hydrogen atom.

Particular emphasis should be placed on compounds of general formula (I), wherein
$R^1$ denotes a phenyl group,
$R^2$ denotes a group selected from among the groups of formulae (i)-(iii) or (v):

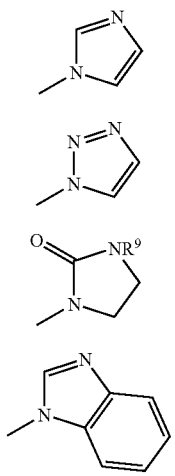

while $R^9$ denotes a phenyl or pyridyl group optionally substituted by a fluorine atom or an amino, nitro, hydroxy or methoxy group,
and the above-mentioned groups (i) to (iii) and (v) may each be substituted by a group $R^{10}$ and
$R^{10}$ denotes an iodine atom or a nitro, amino, methyl, carboxy, methoxycarbonyl, ethoxycarbonyl, pyridin-4-yl, pyridin-2-yl, 6-methoxy-pyridin-3-yl, thiophen-2-yl, 5-methyl-thiophen-2-yl, 3,5-dimethyl-isoxazol-4-yl, 1-acetyl-2-amino-propen-1-yl or a phenyl group, while the phenyl group may be substituted, preferably in the 4 position, by a fluorine atom or by a hydroxy, methoxy, nitro, amino, dimethylamino, methylcarbonylamino, methylsulphonylamino, dimethylamino-sulphonylamino, carboxy, ethoxycarbonyl, benzyloxycarbonyl, hydroxyaminocarbonyl or tetrazol-5-yl group,
$R^3$ and $R^4$ in each case denote a methyl group and
$R^5$, $R^6$ and $R^7$ in each case denote a hydrogen atom,
but especially those compounds of general formula (I), wherein
$R^1$ denotes a phenyl group,
$R^2$ denotes a group of formulae (ia) or (v):

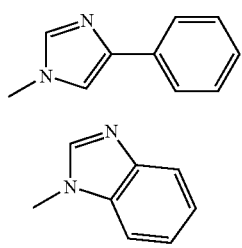

while the above-mentioned group (i) may be substituted in the phenyl moiety by a fluorine atom or by a hydroxy, methoxy, nitro, amino, dimethylamino, methylcarbonylamino, methylsulphonylamino, dimethyl-amino-sulphonylamino, carboxy, ethoxycarbonyl, benzyloxycarbonyl, hydroxyaminocarbonyl or tetrazol-5-yl group and the above-mentioned group (v) may be substituted in the benzyl moiety by a nitro, amino, carboxy or $C_{1-2}$-alkyloxy-carbonyl group,
$R^3$ and $R^4$ each denote a methyl group and
$R^5$, $R^6$ and $R^7$ each denote a hydrogen atom.

The following compounds are particularly preferred:
N-(3-{2-[1,1-dimethyl-3-(4-phenyl-imidazol-1-yl)-propylamino]-1-hydroxy-ethyl}-phenyl)-benzenesulphonamide
N-(3-{2-[1,1-dimethyl-3-(3-methyl-1,4-dioxo-3,4-dihydro-1H-phthalazin-2-yl)-propylamino]-1-hydroxy-ethyl}-phenyl)-benzenesulphonamide
N-(3-{2-[1,1-dimethyl-3-(2-oxo-3-phenyl-imidazolidin-1-yl)-propylamino]-1-hydroxy-ethyl}-phenyl)-benzenesulphonamide
N-[3-(2-{1,1-dimethyl-3-[4-(4-nitro-phenyl)-imidazol-1-yl]-propylamino}-1-hydroxy-ethyl)-phenyl]-benzenesulphonamide
N-[3-(2-{3-[3-(4-fluoro-phenyl)-2-oxo-imidazolidin-1-yl]-1,1-dimethyl-propylamino}-1-hydroxy-ethyl)-phenyl]-benzenesulphonamide
N-[3-(1-hydroxy-2-{3-[4-(4-methoxy-phenyl)-imidazol-1-yl]-1,1-dimethyl-propylamino}-ethyl)-phenyl]-benzenesulphonamide
N-[3-(1-hydroxy-2-{3-[4-(4-hydroxy-phenyl)-imidazol-1-yl]-1,1-dimethyl-propylamino}-ethyl)-phenyl]-benzenesulphonamide
N-[3-(2-{3-[4-(4-amino-phenyl)-imidazol-1-yl]-1,1-dimethyl-propylamino}-1-hydroxy-ethyl)-phenyl]-benzenesulphonamide
N-[3-(1-hydroxy-2-{3-[4-(4-methanesulphonylamino-phenyl)-imidazol-1-yl]-1,1-dimethyl-propylamino}-ethyl)-phenyl]-benzenesulphonamide
N-(3-{1-hydroxy-2-[3-(4-iodo-imidazol-1-yl)-1,1-dimethyl-propylamino]-ethyl}-phenyl)-benzenesulphonamide
methyl 1-{3-[2-(3-benzenesulphonylamino-phenyl)-2-hydroxy-ethylamino]-3-methyl-butyl}-1H-imidazole-4-carboxylate
N-[3-(1-hydroxy-2-{3-[4-(4-N,N-dimethyl-sulphamoylamino-phenyl)-imidazol-1-yl]-1,1-dimethyl-propylamino}-ethyl)-phenyl]-benzenesulphonamide
N-(3-{2-[1,1-dimethyl-3-(2-oxo-3-pyridin-2-yl-imidazolidin-1-yl)-propylamino]-1-hydroxy-ethyl}-phenyl)-benzenesulphonamide
1-{3-[2-(3-benzenesulphonylamino-phenyl)-2-hydroxy-ethylamino]-3-methyl-butyl}-1H-imidazole-4-carboxylic acid
N-(3-{2-[1,1-dimethyl-3-(4-pyridin-4-yl-imidazol-1-yl)-propylamino]-1-hydroxy-ethyl}-phenyl)-benzenesulphonamide
benzyl 4-(1-{3-[2-(3-benzenesulphonylamino-phenyl)-2-hydroxy-ethylamino]-3-methyl-butyl}-1H-imidazol-4-yl)-benzoate
4-(1-{3-[2-(3-benzenesulphonylamino-phenyl)-2-hydroxy-ethylamino]-3-methyl-butyl}-1H-imidazol-4-yl)-benzoic acid
N-[3-(1-hydroxy-2-{3-[3-(4-hydroxy-phenyl)-2-oxo-imidazolidin-1-yl]-1,1-dimethyl-propylamino}-ethyl)-phenyl]-benzenesulphonamide N-[4-(1-{3-[2-(3-benzenesulphonylamino-phenyl)-2-hydroxy-ethylamino]-3-methyl-butyl}-1H-imidazol-4-yl)-phenyl]-acetamide N-[3-(2-{3-[4-(3,5-dimethyl-isoxazol-4-yl)-imidazol-1-yl]-1,1-dimethyl-propylamino}-1-hydroxy-ethyl)-phenyl]-benzenesulphonamide N-[3-(1-hydroxy-2-{3-[4-(6-methoxy-pyridin-3-yl)-imidazol-1-yl]-1,1-dimethyl-propylamino}-ethyl)-phenyl]-benzenesulphonamide N-[3-(2-{1,1-dimethyl-3-[4-(5-methyl-thiophen-2-yl)-imidazol-1-yl]-propylamino}-1-hydroxy-ethyl)-phenyl]-benzenesulphonamide N-[3-(2-{3-[4-(4-fluoro-phenyl)-imidazol-1-yl]-1,1-dimethyl-propylamino}-1-hydroxy-ethyl)-phenyl]-benzenesulphonamide N-(3-{2-[1,1-dimethyl-3-(5-nitro-benzoimidazol-1-yl)-propylamino]-1-hydroxy-ethyl}-phenyl)-benzenesulphonamide N-[3-(1-hydroxy-2-{3-[4-(4-methoxy-phenyl)-[1,2,3]triazol-1-yl]-1,1-dimethyl-propylamino}-ethyl)-phenyl]-benzenesulphonamide N-(3-{2-[1,1-dimethyl-3-(4-thiophen-2-yl-imidazol-1-yl)-propylamino]-1-hydroxy-ethyl}-phenyl)-benzenesulphonamide N-[3-(2-{3-[4-(4-dimethylamino-phenyl)-imidazol-1-yl]-1,1-dimethyl-propylamino}-1-hydroxy-ethyl)-phenyl]-benzenesulphonamide ethyl 4-(1-{3-[2-(3-benzenesulphonylamino-phenyl)-2-hydroxy-ethylamino]-3-methyl-butyl}-1H-imidazol-4-yl)-benzoate N-[3-(1-hydroxy-2-{3-[3-(4-methoxy-phenyl)-2-oxo-imidazolidin-1-yl]-1,1-dimethyl-propylamino}-ethyl)-phenyl]-benzenesulphonamide N-[3-(2-{1,1-dimethyl-3-[3-(4-nitro-phenyl)-2-oxo-imidazolidin-1-yl]-propylamino}-1-hydroxy-ethyl)-phenyl]-benzenesulphonamide N-[3-(1-hydroxy-2-{3-[3-(4-methoxy-phenyl)-5-methyl-[1,2,4]triazol-1-yl]-1,1-dimethyl-propylamino}-ethyl)-phenyl]-benzenesulphonamide N-[3-(2-{3-[3-(4-amino-phenyl)-2-oxo-imidazolidin-1-yl]-1,1-dimethyl-propylamino}-1-hydroxy-ethyl)-phenyl]-benzenesulphonamide N-[3-(2-{3-[4-(1-acetyl-2-amino-propenyl)-imidazol-1-yl]-1,1-dimethyl-propylamino}-1-hydroxy-ethyl)-phenyl]-benzenesulphonamide N-(3-{2-[3-(5-amino-benzoimidazol-1-yl)-1,1-dimethyl-propylamino]-1-hydroxy-ethyl}-phenyl)-benzenesulphonamide 1-{3-[2-(3-benzenesulphonylamino-phenyl)-2-hydroxy-ethylamino]-3-methyl-butyl}-1H-benzoimidazole-5-carboxylic acid ethyl 1-{3-[2-(3-benzenesulphonylamino-phenyl)-2-hydroxy-ethylamino]-3-methyl-butyl}-1H-benzoimidazole-5-carboxylate N-{3-[2-(1,1-dimethyl-3-{4-[4-(1H-tetrazol-5-yl)-phenyl]-imidazol-1-yl}-propylamino)-1-hydroxy-ethyl]-phenyl}-benzenesulphonamide (1-{3-[2-(3-benzenesulphonylamino-phenyl)-2-hydroxy-ethylamino]-3-methyl-butyl}-1H-imidazol-4-yl)-N-hydroxy-benzamide The invention also relates to compounds of general formula (I) for use as pharmaceutical compositions.

The invention also relates to compounds of general formula (I) for use as pharmaceutical compositions with a selective beta-3-agonistic activity.

The invention also relates to compounds of general formula (I) for preparing a pharmaceutical composition for the treatment and/or prevention of diseases connected with the stimulation of beta-3-receptors.

The invention further relates to a method for the treatment and/or prevention of diseases connected with the stimulation of beta-3-receptors, in which a patient is given an effective amount of a compound of general formula I.

The invention further relates to a pharmaceutical composition containing as active substance one or more compounds of general formula (I), optionally combined with conventional excipients and/or carriers.

The invention further relates to a pharmaceutical composition containing as active substance one or more compounds of general formula (I) or the physiologically acceptable salts thereof and one or more active substances selected from among antidiabetics, inhibitors of protein tyrosinephosphatase 1, substances which influence deregulated glucose production in the liver, lipid lowering agents, cholesterol absorption inhibitors, HDL-raising compounds, active substances for the treatment of obesity and modulators or stimulators of the adrenergic system via alpha 1 and alpha 2 as well as beta 1, beta 2 and beta 3 receptors.

The invention further relates to a process for preparing a compound of general formula (I),

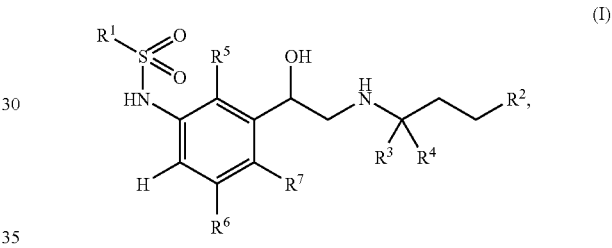

wherein
$R^1$ to $R^7$ may have the meanings given hereinbefore,
where a compound of general formula (II)

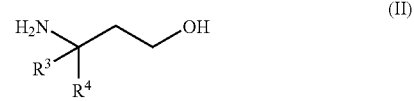

wherein
$R^3$ and $R^4$ may have the meanings given hereinbefore,
is converted by means of a chlorinating agent into a compound of formula (III)

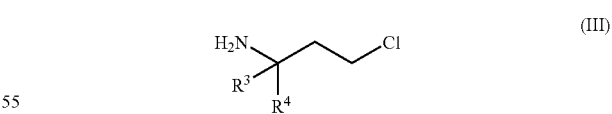

the compound of formula (III), optionally provided with an amino protective group, is reacted with an optionally substituted compound selected from among the following formulae (IV), which may be mono- or polysubstituted by $R^{10}$,

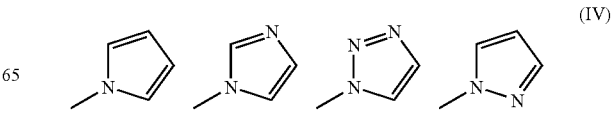

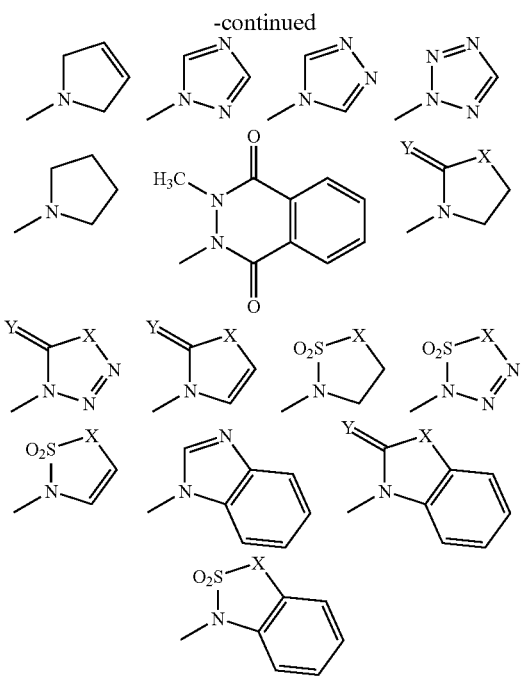

wherein X, Y, Z, $R^9$ and $R^{10}$ may have the meanings given hereinbefore,
and the product of formula (V)

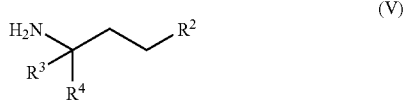

wherein $R^2$, $R^3$ and $R^4$ may have the meanings given hereinbefore,
is reacted with a compound of formula (VIa) or (VIb)

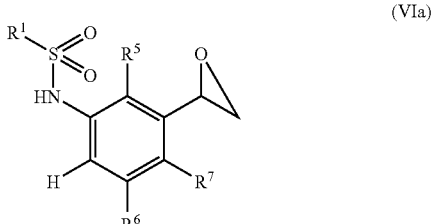

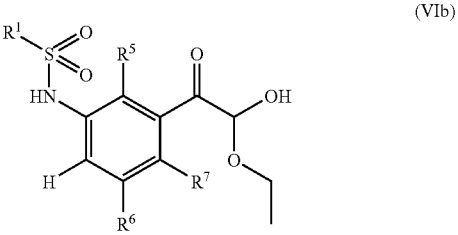

where $R^1$, $R^5$, $R^6$ and $R^7$ may have the meanings given hereinbefore,
while preferably $R^8$ denotes hydrogen or optionally substituted $C_1$-$C_{10}$-alkyl and preferably $R^9$ denotes hydrogen or a group selected from among optionally substituted $C_1$-$C_{10}$-alkyl, $C_3$-$C_8$-cycloalkyl, heterocyclyl, aryl and heteroaryl.

The term alkyl groups, including alkyl groups which are a part of other groups, denotes branched and unbranched alkyl groups with 1 to 10 carbon atoms, while groups with 1 to 6 carbon atoms are preferred. Particularly preferred are alkyl groups with 1 to 4 carbon atoms, particularly those with 1 or 2 carbon atoms. Examples include: methyl, ethyl, propyl, butyl, pentyl, hexyl, heptyl, octyl, nonyl and decyl. Unless otherwise stated, the above-mentioned terms propyl, butyl, pentyl, hexyl, heptyl, octyl, nonyl and decyl include all the possible isomeric forms. For example, the term propyl includes the two isomeric groups n-propyl and iso-propyl, the term butyl includes n-butyl, iso-butyl, sec. butyl and tert.-butyl, the term pentyl includes iso-pentyl, neopentyl, etc.

In the above-mentioned alkyl groups one or more hydrogen atoms may optionally be replaced by other groups. For example, these alkyl groups may be substituted by the halogen atoms fluorine, chlorine, bromine or iodine. Preferably the substituents are fluorine or chlorine. The substituent chlorine is most preferred. All the hydrogen atoms of the alkyl group may optionally also be replaced.

Similarly, in the above-mentioned alkyl groups, unless otherwise stated, one or more hydrogen atoms may optionally be replaced, for example, by OH, $NO_2$, CN or an optionally substituted group selected from among —O—$C_1$-$C_5$-alkyl, preferably methoxy or ethoxy, —O—($C_6$-$C_{14}$-aryl), preferably phenyloxy, —O-heteroaryl, preferably —O-thienyl, —O-thiazolyl, —O-imidazolyl, —O-pyridyl, —O-pyrimidyl or —O-pyrazinyl, saturated or unsaturated —O-heterocycloalkyl, preferably —O-pyrazolyl, —O-pyrrolidinyl, —O-piperidinyl, —O-piperazinyl or —O-tetrahydro-oxazinyl, $C_6$-$C_{14}$-aryl, preferably phenyl, heteroaryl, preferably thienyl, thiazolyl, imidazolyl, pyridyl, pyrimidyl or pyrazinyl, saturated or unsaturated heterocycloalkyl, preferably pyrazolyl, pyrrolidinyl, piperidinyl, piperazinyl or tetrahydro-oxazinyl, an amine group, preferably methylamine, benzylamine, phenylamine or heteroarylamine, saturated or unsaturated bicyclic ring systems, preferably benzimidazolyl and $C_3$-$C_8$-cycloalkyl, preferably cyclohexyl or cyclopropyl.

Alkenyl groups as well as alkenyl groups which are a part of other groups denote branched and unbranched alkyl groups with 1 to 10 carbon atoms, preferably 1 to 6, particularly preferably 1 to 4 carbon atoms, which contain at least one carbon-carbon double bond. Examples include: ethenyl, propenyl, methylpropenyl, butenyl, pentenyl, hexenyl, heptenyl, methylheptenyl, octenyl, nonenyl and decenyl. Unless stated otherwise, the terms propenyl, butenyl, pentenyl, hexenyl, heptenyl, octenyl, nonenyl and decenyl used above include all the possible isomeric forms. For example, the term butenyl includes the isomeric groups but-1-enyl, but-2-enyl and but-3-enyl, etc.

In the above-mentioned alkenyl groups one or more hydrogen atoms may optionally be replaced by other groups. For example, these alkenyl groups may be substituted by the halogen atoms fluorine, chlorine, bromine or iodine. The substituents fluorine or chlorine are preferred. The substituent fluorine is particularly preferred. It is also possible to replace all the hydrogen atoms of the alkenyl group.

Alkynyl groups as well as alkynyl groups which are a part of other groups denote branched and unbranched alkyl groups with 1 to 10 carbon atoms, preferably 1 to 6, particularly preferably 1 to 4 carbon atoms which contain at least one carbon-carbon triple bond. Examples include: ethynyl, propynyl, butynyl, pentynyl, hexynyl, heptynyl, octynyl, nonynyl and decynyl. Unless otherwise mentioned, the terms propynyl, butynyl, pentynyl, hexynyl, heptynyl, octynyl, nonynyl and decynyl used above include all the possible isomeric forms. For example, the term butynyl includes the isomeric groups but-1-ynyl, but-2-ynyl and but-3-ynyl, etc.

In the above-mentioned alkynyl groups one or more hydrogen atoms may optionally be replaced by other groups. For example, these alkynyl groups may be substituted by the halogen atoms fluorine, chlorine, bromine or iodine. The substituents fluorine or chlorine are preferred. The substituent fluorine is particularly preferred. It is also possible to replace all the hydrogen atoms of the alkynyl group.

The term aryl denotes an aromatic ring system with 6 to 18 carbon atoms, preferably 6 to 14 carbon atoms, preferably 6 or 10 carbon atoms, most preferably phenyl, which may optionally be substituted and may preferably carry one or more of the following substituents: OH, $NO_2$, CN, —$OCHF_2$, —$OCF_3$, —$NH_2$, —NH-alkyl, —N(alkyl)-alkyl, —NH-aryl, —N(alkyl)-aryl, —NHCO-alkyl, —NHCO-aryl, —N(alkyl)-CO-alkyl, —N(alkyl)-CO-aryl, —$NHSO_2$-alkyl, —$NHSO_2$—N(alkyl)$_2$, —$NHSO_2$-aryl, —N(alkyl)-$SO_2$-alkyl, —N(alkyl)-$SO_2$-aryl, —$CO_2$-alkyl, —$SO_2$-alkyl, —$SO_2$-aryl, —CONH(OH), —CONH-alkyl, —CONH-aryl, —CON(alkyl)-alkyl, —CON(alkyl)-aryl, —$SO_2$NH-alkyl, —$SO_2$NH-aryl, —$SO_2$N(alkyl)-alkyl, —$SO_2$N(alkyl)-aryl, —O-alkyl, —O-aryl-S-alkyl, —S-aryl, tetrazolyl, halogen, for example fluorine, chlorine, bromine or iodine, preferably fluorine or chlorine, particularly fluorine, $C_1$-$C_{10}$-alkyl, preferably $C_1$-$C_5$-alkyl, particularly preferably $C_1$-$C_3$-alkyl, most particularly preferably methyl or ethyl, —O—($C_1$-$C_3$-alkyl), preferably methoxy or ethoxy, —COOH or —$CONH_2$.

Examples of heteroaryl groups are 5 to 10-membered mono- or bicyclic heteroaryl rings wherein up to three C atoms may be replaced by one heteroatoms selected from among oxygen, nitrogen or sulphur, for example furan, thiophene, pyrrole, pyrazole, imidazole, triazole, tetrazole, pyridine, pyridazine, pyrimidine, pyrazine, triazine, oxazole, isoxazole, thiazole, thiadiazole, oxadiazole, while each of the above-mentioned heterocycles may optionally be annellated to a benzene ring, such as benzimidazole, and these heterocycles may optionally be substituted and preferably carry one or more of the following substituents: OH, $NO_2$, CN, —$NH_2$, —NH-alkyl, —N(alkyl)-alkyl, —NH-aryl, —N(alkyl)-aryl, —NHCO-alkyl, —NHCO-aryl, —N(alkyl)-CO-alkyl, —N(alkyl)-CO-aryl, —$NHSO_2$-alkyl, —$NHSO_2$-aryl, —N(alkyl)-$SO_2$-alkyl, —N(alkyl)-$SO_2$-aryl, —$CO_2$-alkyl, —$SO_2$-alkyl, —$SO_2$-aryl, —CONH-alkyl, —CONH-aryl, —CON(alkyl)-alkyl, —CON(alkyl)-aryl, —$SO_2$NH-alkyl, —$SO_2$NH-aryl, —$SO_2$N(alkyl)-alkyl, —$SO_2$N(alkyl)-aryl, —O-alkyl, —O-aryl-S-alkyl, —S-aryl, —$CONH_2$, halogen, preferably fluorine or chlorine, $C_1$-$C_{10}$-alkyl, preferably $C_1$-$C_5$-alkyl, preferably $C_1$-$C_3$-alkyl, particularly preferably methyl or ethyl, —O—($C_1$-$C_3$-alkyl), preferably methoxy or ethoxy, —COOH, —$COOCH_3$, —$CONH_2$, —SO-alkyl, —$SO_2$-alkyl, —$SO_2$H, —$SO_3$-alkyl or optionally substituted phenyl.

Examples of cycloalkyl groups are saturated or unsaturated cycloalkyl groups with 3 to 8 carbon atoms, for example cyclopropyl, cyclobutyl, cyclopentyl, cyclopentenyl, cyclohexyl, cyclohexenyl, cycloheptyl or cyclooctyl, preferably cyclopropyl, cyclopentyl or cyclohexyl, while each of the above-mentioned cycloalkyl groups may optionally also carry one or more substituents or be annellated to a benzene ring.

Unless otherwise stated in the definitions, examples of heterocycloalkyl or heterocyclyl groups include 5-, 6- or 7-membered, saturated or unsaturated heterocycles which may contain nitrogen, oxygen or sulphur as heteroatoms, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole and pyrazolidine, preferably pyrazolyl, pyrrolidinyl, piperidinyl, piperazinyl or tetrahydro-oxazinyl, while the heterocyclic group may optionally be substituted.

The compounds of the above general formula (I) which contain a group that can be cleaved in-vivo are so-called prodrugs, and compounds of general formula I which contain two groups that can be cleaved in-vivo are so-called double prodrugs.

By a group which can be converted in-vivo into a carboxy group is meant for example an ester of formula —$CO_2R^{11}$, where $R^{11}$ denotes hydroxymethyl, alkenyl, alkynyl, aryl, heteroaryl, cycloalkenyl, heterocycloalkyl, $C_1$-$C_3$-alkoxycarbonyl, 1,3-dihydro-3-oxo-1-isobenzofuranol, —C(-alkyl)(-alkyl)-OC(O)-alkyl, —CHC(O)NH(-alkyl), —CHC(O)N(-alkyl)(-alkyl), -alkyl, preferably $C_1$-$C_6$-alkyl, particularly preferably methyl, ethyl, n-propyl, iso-propyl, n-butyl, n-pentyl or n-hexyl, cycloalkyl, preferably $C_1$-$C_6$-cycloalkyl, particularly preferably cyclohexyl, —($C_1$-$C_3$-alkyl)-aryl, preferably ($C_1$-$C_3$-alkyl)-phenyl, particularly preferably benzyl, —CHC(O)N(-alkyl)(-alkyl), preferably —CHC(O)N(—$C_1$-$C_3$-alkyl)(—$C_1$-$C_3$-alkyl), particularly preferably —CHC(O)N($CH_3$)$_2$, —CH(-alkyl)OC(O)-alkyl, preferably —CH(—$CH_3$)OC(O)(—$C_1$-$C_6$-alkyl), particularly preferably —CH(—$CH_3$)OC(O)-methyl, —CH(—$CH_3$)OC(O)-ethyl, —CH(—$CH_3$)OC(O)-n-propyl, —CH(—$CH_3$)OC(O)-n-butyl or —CH(—$CH_3$)OC(O)-t-butyl, or —$CH_2$OC(O)-alkyl, preferably —$CH_2$OC(O)(—$C_1$-$C_6$-alkyl), particularly preferably —$CH_2$OC(O)-methyl, —$CH_2$OC(O)-ethyl, —$CH_2$OC(O)-n-propyl, —$CH_2$OC(O)-n-butyl or —$CH_2$OC(O)-t-butyl.

By a group which can be converted in-vivo into a sulphonamide or amino group is meant for example one of the following groups:

—OH, -formyl, —C(O)-alkyl, —C(O)-aryl, —C(O)-heteroaryl, —$CH_2$OC(O)-alkyl, —CH(-alkyl)OC(O)-alkyl, —C(-alkyl)(-alkyl)OC(O)-alkyl, —$CO_2$-alkyl, preferably $C_1$-$C_9$-alkoxy-carbonyl, particularly preferably methoxycarbonyl, ethoxycarbonyl, n-propyloxycarbonyl, isopropyloxycarbonyl, n-butyloxycarbonyl, n-pentyloxycarbonyl, n-hexyloxycarbonyl, cyclohexyloxycarbonyl, n-heptyloxycarbonyl, n-octyloxycarbonyl or n-nonyloxycarbonyl, —$CO_2$(—$C_1$-$C_3$-alkyl)-aryl, preferably —$CO_2$(—$C_1$-$C_3$-alkyl)-phenyl, particularly preferably benzyloxycarbonyl, —C(O)-aryl, preferably benzoyl, —C(O)-heteroaryl, preferably pyridinoyl or nicotinoyl or —C(O)-alkyl, preferably —C(O)(—$C_1$-$C_6$-alkyl), particularly preferably 2-methyl-sulphonylethoxycarbonyl-, 2-(2-ethoxy)-ethoxycarbonyl-.

Halogen generally denotes fluorine, chlorine, bromine or iodine, preferably chlorine or fluorine, particularly preferably fluorine.

The compounds according to the invention may be in the form of the individual optical isomers, mixtures of the individual enantiomers, diastereomers or racemates, prodrugs, double prodrugs and in the form of the tautomers, salts, solvates and hydrates as well as in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic, formic, malic, benzoic, benzenesulphonic, camphorsulphonic, acetic, ethanesulphonic, glutamic, maleic, mandelic, lactic, phosphoric, nitric, sulphuric, succinic, para-toluenesulphonic, trifluoroacetic, tartaric, citric or methanesulphonic acid.

Moreover, if the new compounds of formula I thus obtained contain a carboxy group or another acid group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

Moreover the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

The substituent $R^1$ may represent optionally substituted aryl or heteroaryl, preferably substituted phenyl. Particularly preferably, the substituent $R^1$ denotes phenyl.

The substituent $R^2$ may represent a heteroaryl or heterocyclyl mono- or polysubstituted by $R^{10}$, where $R^2$ contains at least one nitrogen atom. Particularly preferred is a triazole mono- or polysubstituted by $R^{10}$, a 1,4-dioxo-3,4-dihydro-1H-phthalazine mono- or polysubstituted by $R^{10}$, a 2-oxoimidazolidine mono- or polysubstituted by $R^{10}$, a benzimidazole mono- or polysubstituted by $R^{10}$ or an imidazole mono- or polysubstituted by $R^{10}$.

Most particularly preferred meanings of the substituent $R^2$ are a 1H-[1,2,3]triazol-1-yl monosubstituted by $R^{10}$, a 1,4-dioxo-3,4-dihydro-1H-phthalazin-2-yl monosubstituted by $R^{10}$, a 2-oxo-imidazolidin-1-yl monosubstituted by $R^{10}$, a benzimidazol-1-yl monosubstituted by $R^{10}$ or an imidazol-1-yl monosubstituted by $R^{10}$.

The substituents $R^3$ and $R^4$ may independently of one another represent hydrogen or an optionally substituted group selected from among $C_3$-$C_6$-cycloalkyl or $C_1$-$C_5$-alkyl, preferably $C_1$-$C_5$-alkyl, or $R^3$ and $R^4$ together represent a 2- to 7-membered alkylene bridge, preferably a 2- to 5-membered alkylene bridge, particularly an ethylene bridge.

A substituted $R^3$ or $R^4$ is preferably substituted by $C_1$-$C_3$-alkyl.

Preferably $R^3$ denotes methyl.

Preferably $R^4$ denotes methyl.

The substituents $R^5$, $R^6$ and $R^7$ may independently of one another denote hydrogen or a group selected from among halogen, cyano, —$NR^8$CO—($C_1$-$C_5$-alkyl), —$NR^8$CO-aryl, —$NR^8SO_2$—($C_1$-$C_5$-alkyl), —$NR^8SO_2$-aryl, —$CO_2R^8$, —$SO_2R^8$, —$CONHR^8$, —$SO_2NHR^8$, —$OR^8$, optionally substituted $C_3$-$C_6$-cycloalkyl and optionally substituted $C_1$-$C_{10}$-alkyl, preferably hydrogen, halogen, cyano, methoxy, methanesulphonylamino, methanesulphonyl, difluoromethoxy, trifluoromethoxy, difluoromethyl or trifluoromethyl, particularly hydrogen, fluorine, chlorine or cyano. A most particularly preferred definition of the substituents $R^5$, $R^6$ and $R^7$ is hydrogen.

The substituent $R^8$ may represent hydrogen or $C_1$-$C_5$-alkyl, preferably methyl.

The substituent $R^9$ may represent hydrogen, optionally substituted aryl or optionally substituted heteroaryl, preferably optionally substituted phenyl, pyridyl or thiophenyl.

The substituent $R^{10}$ may represent OH, $NO_2$, CN, —$OCHF_2$, —$OCF_3$, —$NH_2$, —NH-alkyl, —N(-alkyl)-alkyl, —NH-aryl, —N(-alkyl)-aryl, —NHCO-alkyl, —NHCO-aryl, —N(-alkyl)CO-alkyl, —N(-alkyl)CO-aryl, —$NHSO_2$-alkyl, —$NHSO_2$-aryl, —N(-alkyl)$SO_2$-alkyl, —N(-alkyl)-$SO_2$-aryl, —$CO_2$-alkyl, —$SO_2$-alkyl, —$SO_2$-aryl, —CONH-alkyl, —CONH-aryl, —CON(-alkyl)-alkyl, —CON(-alkyl)-aryl, —$SO_2$NH-alkyl, —$SO_2$NH-aryl, —$SO_2$N(-alkyl)-alkyl, —$SO_2$N(-alkyl)-aryl, —O-alkyl, —O-aryl, —S-alkyl, —S-aryl, halogen, $C_1$-$C_{10}$-alkyl, —O—($C_1$-$C_3$-alkyl), —COOH, —$CONH_2$, —CON(-alkyl)$SO_2$-alkyl, —$CONHSO_2$-alkyl, —CONHOH, 2,5-dihydro-5-oxo-4H-1,2,4-oxadiazol-3-yl, 2,5-dihydro-5-oxo-4H-1,2,4-thiadiazol-3-yl, 2,5-dihydro-2-oxo-3H-1,2,4,5-oxathiadiazol-4-yl, tetrazolyl, heterocyclyl, aryl or heteroaryl.

Preferably $R^{10}$ denotes —OH, —$NO_2$, —CN, —$NH_2$, —I, —$N(CH_3)_2$, —$NHCO_2CH_3$, —$NHSO_2CH_3$, —$SO_2N(CH_3)_2$, —$CO_2H$, benzyloxycarbonyl, ethoxycarbonyl, methoxycarbonyl, —CONHOH, tetrazol-5-yl, pyridin-4-yl, pyridin-2-yl, 6-methoxy-pyridin-3-yl, phenyl, 4-hydroxyphenyl, 4-fluorophenyl, 4-methoxy-phenyl, 4-aminophenyl, 4-nitrophenyl, thiophen-2-yl, 5-methyl-thiophen-2-yl, 3,5-dimethyl-isoxazol-4-yl or 1-acetyl-2-amino-propenyl.

The compounds according to the invention may be prepared by the methods of synthesis described below, while formulae (I) to (VI) and the substituents of general formulae $R^1$ to $R^7$ have the meanings given hereinbefore. These methods are intended as an illustration of the invention without restricting it to their content.

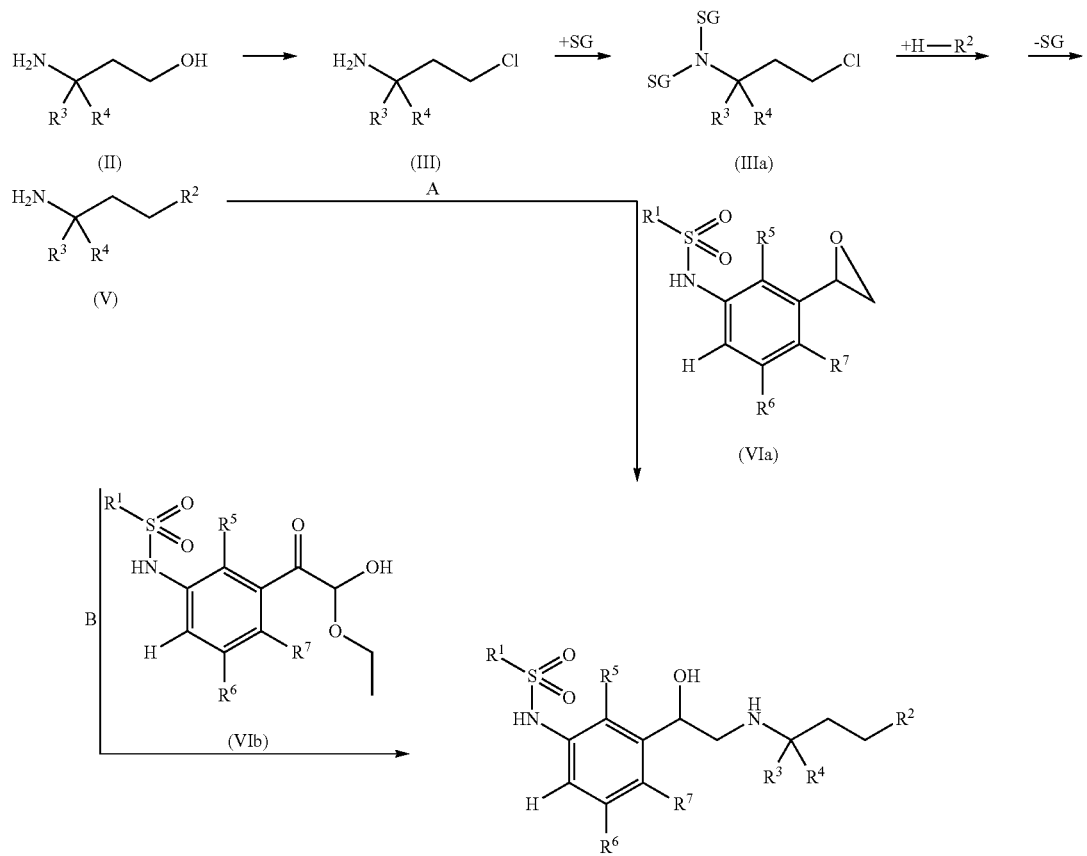

SG = Schutzgruppe   SG = protective group

General Methods of Synthesis

Synthesis of the 3-chloropropylamine-hydrochlorides

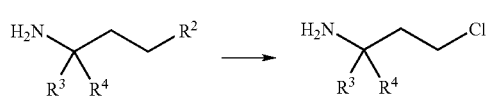

130 mmol thionyl chloride were slowly added dropwise at 0° C. to a solution of 100 mmol 3-aminobutanoyl in 50 mL methylene chloride/dimethylformamide (50:1) with vigorous stirring. After the addition had ended the reaction mixture was refluxed for about 1 hour (h) at reflux temperature and then stirred for about 16 h at ambient temperature. The solvent was removed and the residue was combined with 10 mL acetonitrile with stirring. The solid was filtered off and dried.

Synthesis of the tert-butyl (3-chloropropyl)-carbamates

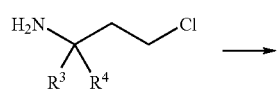

-continued

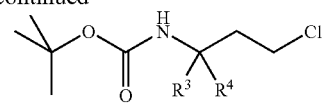

100 mmol di-tert.-butyldicarbonate were added batchwise to a solution of 140 mmol 3-chloropropylamine hydrochloride and 330 mmol triethylamine in 400 mL methylene chloride at ambient temperature with vigorous stirring. After the addition had ended the reaction mixture was stirred for about 4 days (d) at ambient temperature (RT). The solvent was removed and the residue was taken up in about 100 mL ethyl acetate and about 200 mL water. The phases were separated and the aqueous phase was extracted twice with about 100 mL ethyl acetate. The combined organic phases were washed about three times with 100 mL water, dried over sodium sulphate and the solvent was eliminated using the rotary evaporator.

Synthesis of the Substituted tert-butyl (3-aminopropyl)-carbamates

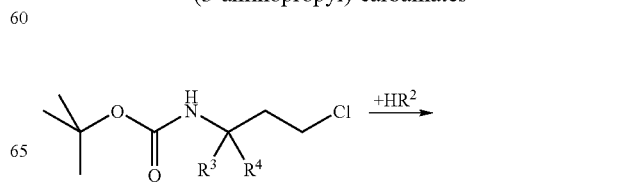

-continued

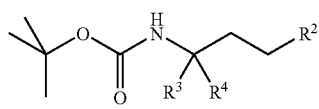

11 mmol sodium hydride were added batchwise at 5° C. to a solution of 10 mmol HR² in 15 mL of 1,3-dimethyl-3,4,5,6-tetrahydro-2(1H)-pyrimidone, with vigorous stirring. After the development of gas had ended the reaction mixture was stirred for about 1 h at 0° C. and 10 mmol tert-butyl (3-chloropropyl)-carbamate in 5 mL 1,3-dimethyl-3,4,5,6-tetrahydro-2(1H)-pyrimidone and 1 mmol tetrabutylammonium iodide were added. The reaction mixture was stirred for approx. 48 h at ambient temperature and then poured into 450 mL ice water/ethyl acetate 2:1. The phases were separated and the aqueous phase was extracted about three times with 100 mL ethyl acetate. The combined organic phases were washed about five times with 100 mL water, then with about 100 mL saturated, aqueous sodium chloride solution, dried and freed from the solvent. The residue was purified by flash column chromatography.

Synthesis of the Substituted Amines

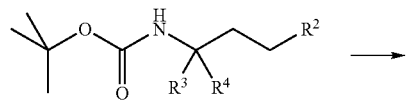

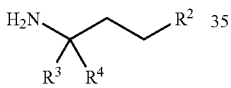

2 mL trifluoroacetic acid were added to a solution of 1 mmol) tert-butyl {3-[3-(4-fluoro-phenyl)-2-oxo-imidazolidin-1-yl]-1,1-dimethyl-propyl}-carbamate in 5 mL dichloromethane at ambient temperature with vigorous stirring. The reaction mixture was stirred for approx. 16 h at ambient temperature and then freed from the solvent. The residue was stirred with diethyl ether or purified by flash column chromatography.

The free base was prepared from the amine-bistrifluoroacetate obtained using known methods.

Synthesis Route A):

Synthesis of the Substituted 2-chloro-1-phenylethanones

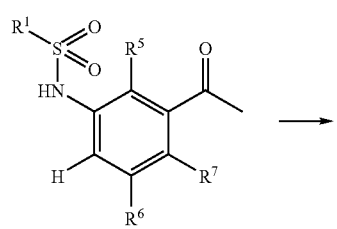

-continued

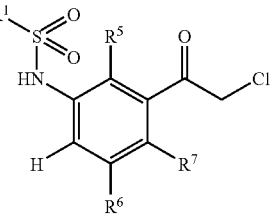

30 mmol sulphuryl chloride were added dropwise with vigorous stirring to a solution of 10 mmol 1-phenylethanone in about 50 mL dichloromethane at 0° C. over approx. 30 min. The reaction mixture was refluxed for approx. 3 h, cooled to ambient temperature and washed with about 50 mL water, about 50 mL saturated, aqueous sodium hydrogen carbonate solution and about 50 mL saturated aqueous sodium chloride solution. The organic phase was dried and freed from the solvent.

Synthesis of the Substituted 2-chloro-1-phenyl-ethanols

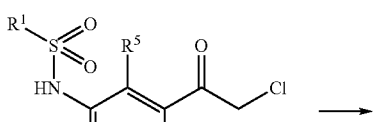

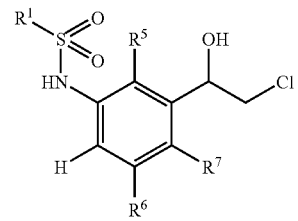

11 mmol borane-tetrahydrofuran complex (1M in tetrahydrofuran) were added dropwise at 10° C. with vigorous stirring over approx. 30 min to a solution of 10 mmol 2-chloro-1-phenylethanone in about 25 mL tetrahydrofuran. After the development of gas had ended the reaction was stirred for approx. 16 h at ambient temperature and then poured into about 450 mL water/ethyl acetate 2:1. The phases were separated and the aqueous phase was extracted about three times with 100 mL ethyl acetate. The combined organic phases were washed about twice with 100 mL water, then with about 100 mL saturated, aqueous sodium chloride solution, dried and freed from the solvent. The residue was purified by flash column chromatography By using an enantioselective reducing agent (Shinichi, I., *Organic Reactions* 1998, 52, 395-576; Wallabaum, S.; Martens, J. *Tetrahedron: Asymmetry* 1992, 3, 1475-1504; Hett, R.; Senanayake, C. H.; Wald, S. A. *Tetrahedron Letters* 1998, 39, 1705-1708; Yaozhong, J.; Yong, Q.; Aiqiao, M.; Zhitang, M. *Tetrahedron: Asymmetry* 1994, 5, 1211-1214; Sawa, I.; Konishi, Y.; Maemoto, S.; Hasegawa, J. WO 9201804A1, 1992; Yasohara, Y.; Ueda, M.; Hasegawa, J.; Shimizu, A.; Kataoka, M.; Wada M.; Kawabata, J. JP 11215995, 1999; Hamada, T.; Torii, T.; Izawa, K.; Noyori, R.;

Ikariya, T. *Organic Letters* 2002, 4, 4373-4376) the 2-chloro-1-phenylethanols may also be obtained in enantiomerically pure form. The (R)-enantiomers are of outstanding importance according to the invention.

Synthesis of the Substituted Phenyloxirans

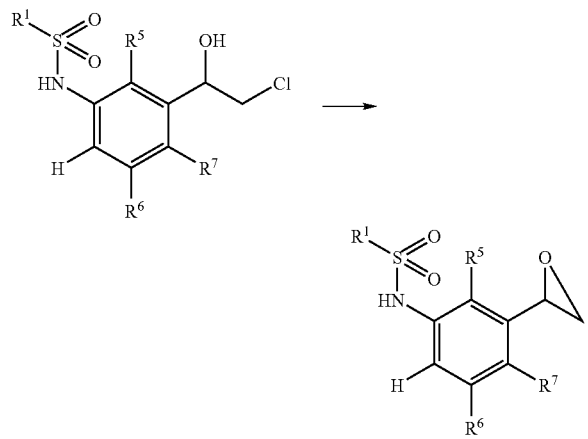

13 mmol potassium carbonate and 2 mmol sodium iodide were added to a solution of 10 mmol 2-chloro-1-phenylethanol in about 30 mL acetonitrile. The reaction mixture was refluxed for approx. 8 h and then poured into about 150 mL water/ethyl acetate 2:1. The phases were separated and the aqueous phase was extracted about three times with 50 mL ethyl acetate. The combined organic phases were washed with about 50 mL water, then with about 50 mL saturated, aqueous sodium chloride solution, dried and freed from the solvent. The residue was purified by flash column chromatography.

Synthesis of the Substituted Phenyloxiran (R)-Enantiomers

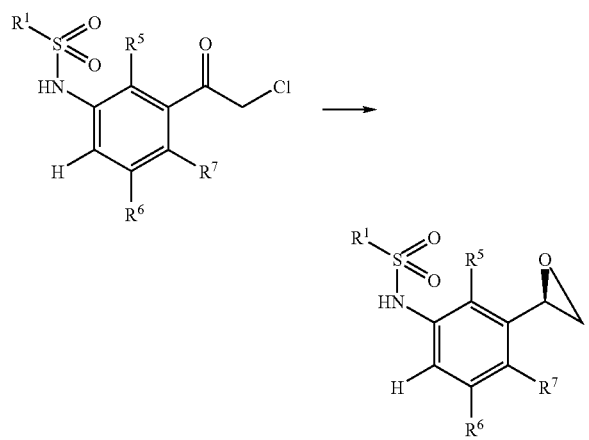

Carried out analogously to a process described in the literature (Org. Lett. 2002, 4, 4373-4376).

6 mL of a mixture of formic acid and triethylamine (molar ratio=5:2) are added dropwise at 0° C. to a solution of 30 mmol of a substituted 2-chloro-1-phenylethanone and 0.03 mmol Cp*RhCl[(S,S)-TsDPEN] (Cp*=pentamethylcyclopentadienyl and TsDPEN=(1S,2S)—N-p-toluenesulphonyl-1,2-diphenylethylenediamine) in 15 mL dimethylformamide. The mixture is stirred for 24 h at 0° C. and 45 mg catalyst and 6 mL of a mixture of formic acid and triethylamine (molar ratio=5:2) are added thereto. After another 2.5 h stirring at 0° C. the reaction mixture is combined at 0° C. with 33.9 mL sodium hydroxide solution. The reaction mixture is stirred for 1.5 h at 0° C., acidified with 13.5 mL glacial acetic acid and extracted about three times with ethyl acetate. The combined organic phases were washed about three times with water and then with saturated, aqueous sodium chloride solution, dried over sodium sulphate and freed from the solvent. The residue was purified by flash column chromatography.

The further reactions are carried out analogously in each case: starting from racemic educts racemic products are obtained and starting from enantiomerically pure compounds enantiomerically pure products are obtained. Alternatively, a racemic end compound obtained may be separated into the two enantiomers for example by chiral column chromatography or by recrystallisation with suitable chiral counter-ions.

Synthesis of the Substituted Ethanolamines

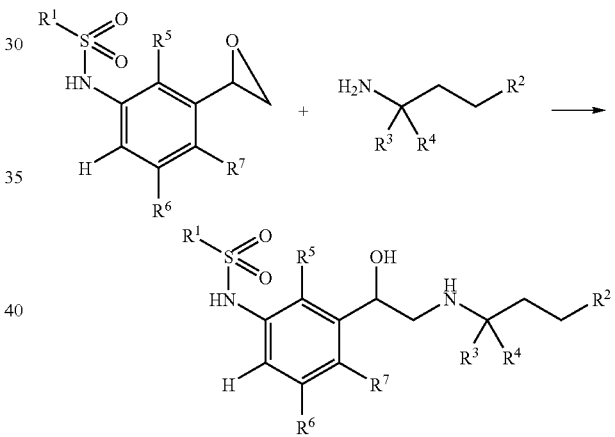

1 mmol phenyloxiran was added to a solution of 1 mmol amine in 2 mL ethanol and refluxed for approx. 18 h. The reaction mixture was freed from the solvent and the residue was purified by flash column chromatography or recrystallisation. The free ethanolamine or the corresponding salt was obtained as a solid.

Synthesis Route B):

Synthesis of the Substituted ethoxy-hydroxyketones

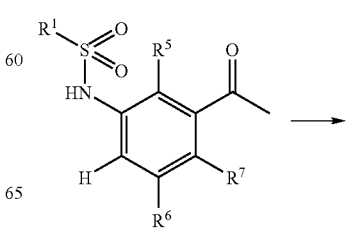

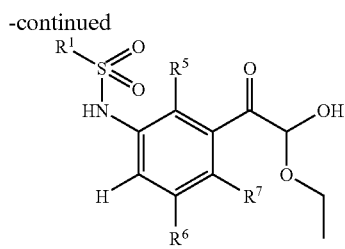

5 ml of water, 5 g activated charcoal and 60 mmol selenium dioxide were added to a solution of 30 mmol 1-phenylethanone in about 50 mL dioxane. The reaction mixture was stirred for approx. 20 h at 80° C. and then the solvent was eliminated using the rotary evaporator. The residue was dissolved in about 30 ml of ethanol and refluxed for approx. 6 h. The reaction mixture was freed from the solvent, dissolved in about 150 mL ethyl acetate, washed about three times with 100 ml saturated, aqueous sodium hydrogen carbonate solution, dried and the solvent was eliminated using the rotary evaporator. The residue was purified by flash column chromatography.

Synthesis of the Substituted Ethanolamines

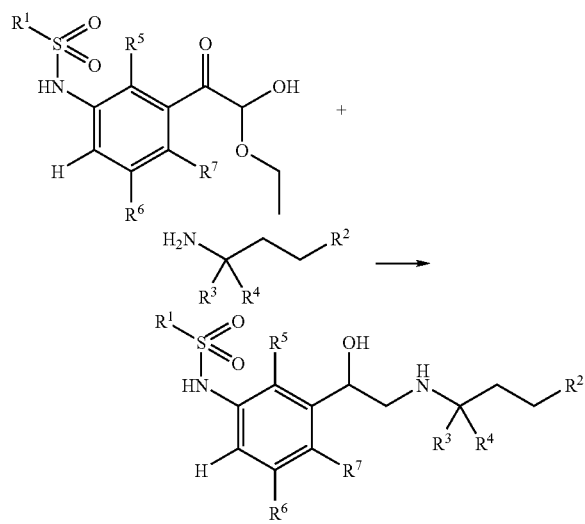

1 mmol ethoxy-hydroxyketone was added to 1 mmol amine bistrifluoroacetate in 10 mL ethanol and refluxed for approx. 18 h. The reaction mixture was cooled to 0° C. and then combined with 3 mmol sodium borohydride. It was stirred for approximately another 3 h at ambient temperature and then combined with 20 mL saturated, aqueous potassium carbonate solution and 20 mL ethyl acetate. The phases were separated and the aqueous phase was extracted with ethyl acetate. The combined organic phases were washed with saturated, aqueous sodium chloride solution, dried and freed from the solvent. The residue was purified by flash column chromatography or recrystallisation. The free ethanolamine or the corresponding salt was thus obtained as a solid.

Suzuki Coupling of Substituted Iodoimidazoles with Substituted Boric Acids 1 mmol iodoimidazole, 2 mmol arylboric acid, 0.01 mmol tetrakis(triphenylphosphino)palladium and 0.01 mmol tetrabutylammonium bromide in 20 mL saturated aqueous sodium hydrogen carbonate solution/toluene (1:1) were refluxed for approx. 3 d. The reaction mixture was combined at ambient temperature with about 100 mL toluene water (1:1), the phases were separated and the organic phase was washed about three times with 50 mL water. The organic phase was dried and freed from the solvent. The residue was purified by flash column chromatography. The desired phenylimidazole was obtained as a colourless oil.

The new compounds of general formula (I) may be synthesised analogously to the following examples of synthesis. These Examples are intended purely as a further illustration of the invention without restricting it to their content.

Example 22

Synthesis of N-[3-(2-ethoxy-2-hydroxyacetyl)-phenyl]-benzenesulphonamide

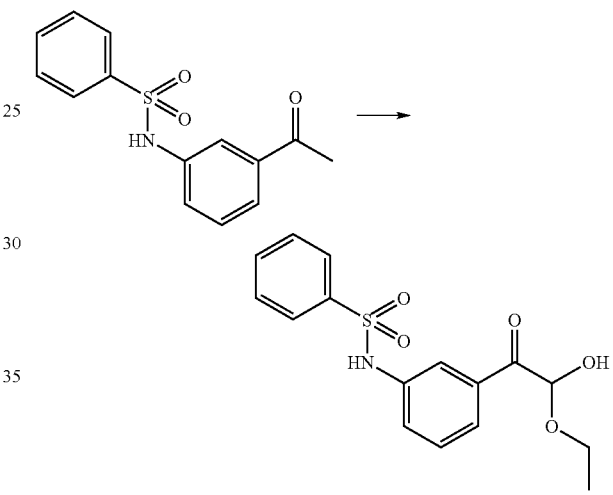

1 ml of water, 1 g activated charcoal and 2.66 g (24 mmol) selenium dioxide was added to a solution of 1.65 g (6.00 mmol) N-(acetylphenyl)benzenesulphonamide in about 10 mL dioxane. The reaction mixture was stirred for approx. 4 d at 80° C. and then the solvent was eliminated using the rotary evaporator. The residue was dissolved in about 30 ml of ethanol and refluxed for approx. 4 h. The solvent was eliminated from the reaction mixture using the rotary evaporator, the residue was dissolved in about 100 mL ethyl acetate, washed about three times with 30 ml saturated aqueous sodium hydrogen carbonate solution, dried over sodium sulphate and the solvent was eliminated using the rotary evaporator. 0.917 g (2.73 mmol, 46%) N-[3-(2-ethoxy-2-hydroxyacetyl)-phenyl]-benzenesulphonamide were obtained as a yellow solid.

Synthesis of 3-chloro-1,1-dimethylpropylamine-hydrochloride

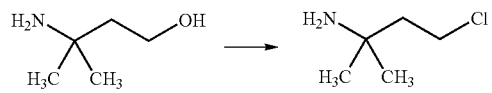

48.7 mL (668 mmol) thionyl chloride were slowly added dropwise at 0° C. with vigorous stirring to a solution of 53.0 g (514 mmol) 3-amino-3-methyl-butanol in 255 mL methylene chloride/dimethylformamide (50:1). After the addition had ended the reaction mixture was refluxed for 1 h at reflux temperature and then stirred for 16 h at ambient temperature. The solvent was removed and the residue was combined with 50 mL acetonitrile with stirring. The solid was filtered off and dried for 18 h at 45° C. 67.9 g (430 mmol, 84%) 3-chloro-1,1-dimethylpropylamine-hydrochloride were obtained as a colourless solid.

Synthesis of tert-butyl
(3-chloro-1,1-dimethyl-propyl)-carbamate

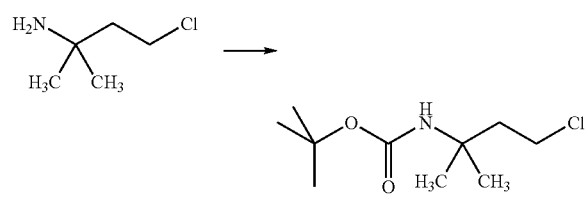

101 g (218 mmol) di-tert.-butyldicarbonate were added batchwise to a solution of 48.8 g (309 mmol) 3-chloro-1,1-dimethylpropylamine-hydrochloride and 100 mL (718 mmol) triethylamine in 900 mL methylene chloride, at ambient temperature, with vigorous stirring. After the addition had ended the reaction was stirred for 4 d at RT. The solvent was removed and the residue was taken up in 250 mL ethyl acetate and 400 mL water. The phases were separated and the aqueous phase was extracted twice with 200 mL ethyl acetate. The combined organic phases were washed three times with 150 mL water, dried over sodium sulphate and the solvent was eliminated using the rotary evaporator. 45.3 g (204 mmol, 66%) tert-butyl (3-chloro-1,1-dimethyl-propyl)-carbamate were obtained as a colourless oil.

Synthesis of tert-butyl [3-(4-iodo-imidazol-1-yl)-1,1-dimethyl-propyl]-carbamate

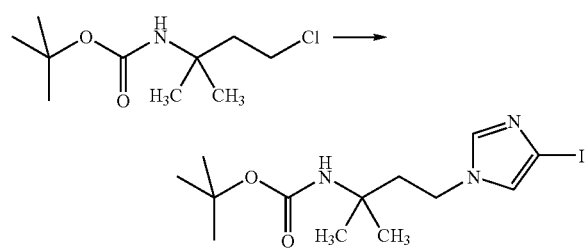

0.556 g (22.0 mmol) sodium hydride were added batchwise to a solution of 3.88 g (20.0 mmol) iodoimidazole in 30 mL 1,3-dimethyl-3,4,5,6-tetrahydro-2(1H)-pyrimidone at 5° C. with vigorous stirring. After the development of gas had ended the reaction was stirred for 1 h at 0° C. and 4.44 g (20 mmol) tert-butyl (3-chloro-1,1-dimethyl-propyl)-carbamate in 5 mL 1,3-dimethyl-3,4,5,6-tetrahydro-2(1H)-pyrimidone and 0.739 g (2.00 mmol) tetrabutylammonium iodide were added. The reaction mixture was stirred for 16 h at ambient temperature, stirred for 24 h at 80° C., cooled to ambient temperature and poured into 750 mL ice water/ethyl acetate 2:1. The phases were separated and the aqueous phase was extracted three times with 150 mL ethyl acetate. The combined organic phases were washed five times with 150 mL water, then once with 150 mL saturated, aqueous sodium chloride solution, dried over sodium sulphate and the solvent was eliminated using the rotary evaporator. The residue was purified by flash column chromatography [petroleum ether/ethyl acetate (80:20→0:100)]. 3.19 g (8.40 mmol, 42%) tert-butyl [3-(4-iodo-imidazol-1-yl)-1,1-dimethyl-propyl]-carbamate were obtained as a colourless oil.

Synthesis of
3-(4-iodo-imidazol-1-yl)-1,1-dimethyl-propylamine

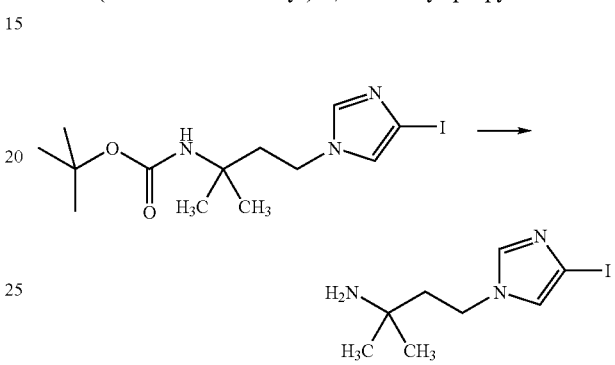

10 mL (130 mmol) trifluoroacetic acid were added to a solution of 1.90 g (5.00 mmol) tert-butyl [3-(4-iodo-imidazol-1-yl)-1,1-dimethyl-propyl]-carbamate in 90 mL dichloromethane at ambient temperature with vigorous stirring. The reaction mixture was stirred for 16 h at ambient temperature and the solvent was eliminated using the rotary evaporator. The residue was taken up in 100 mL sodium hydroxide solution (1M) and 100 mL dichloromethane. The phases were separated and the aqueous phase was extracted three times with 100 mL dichloromethane. The combined organic phases were dried over magnesium sulphate and the solvent was eliminated using the rotary evaporator. 1.37 g (4.91 mmol, 98%) 3-(4-iodo-imidazol-1-yl)-1,1-dimethyl-propylamine were obtained as a colourless oil.

Synthesis of N-(3-{1-hydroxy-2-[3-(4-iodo-imidazol-1-yl)-1,1-dimethyl-propylamino]-ethyl}-phenyl)-benzenesulphonamide (Example 10)

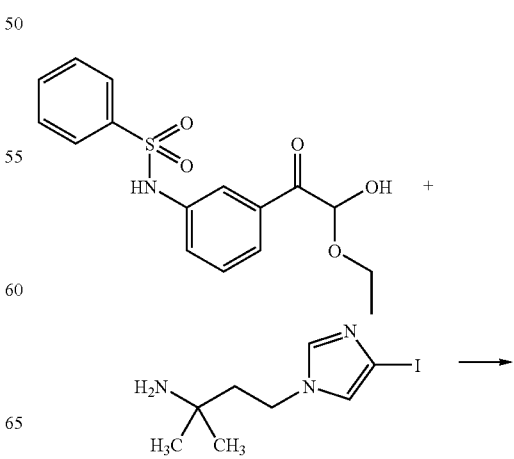

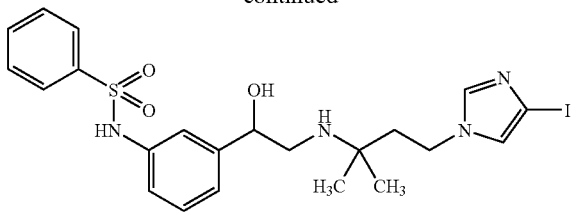

7.81 g (23.3 mmol) N-[3-(2-ethoxy-2-hydroxy-acetyl)-phenyl]-benzenesulphonamide and 6.50 g (23.3 mmol) 3-(4-iodo-imidazol-1-yl)-1,1-dimethyl-propylamine in 40 mL ethanol were refluxed for 15 h. The reaction mixture was cooled to 0° C. and then combined with 3.70 g (97.9 mmol) sodium borohydride. It was stirred for a further 24 h at ambient temperature stirred and then combined with 20 mL saturated aqueous potassium carbonate solution. The aqueous phase was separated from the organic phase and extracted twice with 50 mL ethyl acetate. The combined organic phases were washed with 20 mL saturated, aqueous sodium chloride solution, dried over magnesium sulphate and freed from the solvent using the rotary evaporator. The residue was purified by flash column chromatography [methylene chloride/methanol/ammonia (90:10:1)]. 12.9 g (10.5 mmol, 45%) N-(3-{1-hydroxy-2-[3-(4-iodo-imidazol-1-yl)-1,1-dimethyl-propylamino]-ethyl}-phenyl)-benzenesulphonamide were obtained as a colourless solid.

Synthesis of N-[3-(2-{1,1-dimethyl-3-[4-(5-methyl-thiophen-2-yl)-imidazol-1-yl]-propylamino}-1-hydroxy-ethyl)-phenyl]-benzenesulphonamide (Suzuki Coupling)

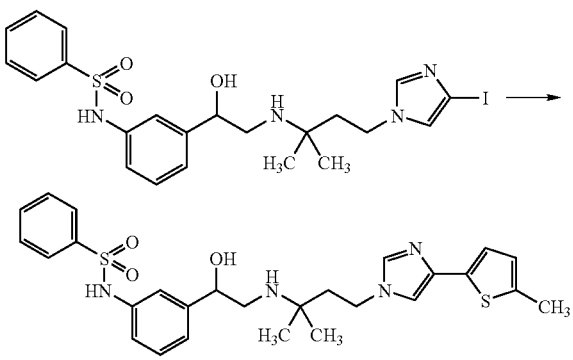

0.277 g (0.500 mmol) N-(3-{1-hydroxy-2-[3-(4-iodo-imidazol-1-yl)-1,1-dimethyl-propylamino]-ethyl}-phenyl)-benzenesulphonamide, 0.807 g (0.613 mmol) 5-methylthiophene-2-boric acid, 0.031 g (0.038 mmol) [1,1'-bis(diphenylphosphino)ferrocene]-palladium(II)-chloride (1:1 complex with dichloromethane), 2.00 mL aqueous sodium carbonate solution (2M) and 2 mL dioxane were stirred for 5 min at 150° C. in a sealed reaction vessel in a microwave. The reaction mixture was cooled to ambient temperature and then poured into 20 mL dichloromethane and 20 mL water. The phases were separated, the organic phase was washed twice with 20 mL water, dried over magnesium sulphate and the solvent was eliminated using the rotary evaporator. The residue was purified by flash column chromatography [methylene chloride/methanol (100:0→75:25)]. 0.200 g (0.381 mmol, 76%) N-[3-(2-{1,1-dimethyl-3-[4-(5-methyl-thiophen-2-yl)-imidazol-1-yl]-propylamino}-1-hydroxy-ethyl)-phenyl]-benzenesulphonamide were obtained as a beige solid.

Examples 4, 9, 16, 19, 20, 21, 23, 26, 27, 28 and 38 were synthesised analogously to the method described for Example 22. In the last step of the reaction, the following reagents were used instead of 5-methylthiophene-2-boric acid.

Example 4

4-nitrophenylboric acid

Example 9

4-methanesulphonylaminoboric acid

Example 16

4-benzyloxycarbonylphenylboric acid

Example 19

4-acetamidophenylboric acid

Example 20

3,5-dimethylisoxazole-4-boric acid

Example 21

2-methoxy-5-pyridineboric acid

Example 23

4-fluorophenylboric acid

Example 26 thiophene-2-boric acid

Example 27

4-(N,N-dimethylamino)phenylboric acid

Example 28

4-ethoxycarbonylphenylboric acid

Example 38

4-tetrazolylphenylboric acid (Organic Letters 6 (2004) 19, 3265-3268)

Example 14

Synthesis of methyl 1-{3-[2-(3-benzenesulphonylamino-phenyl)-2-hydroxy-ethylamino]-3-methyl-butyl}-1H-imidazole-4-carboxylate (Example 11)

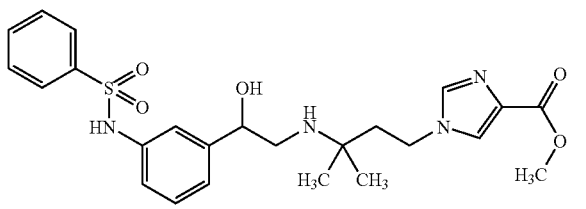

0.554 g (1.00 mmol) N-(3-{1-hydroxy-2-[3-(4-iodo-imidazol-1-yl)-1,1-dimethyl-propylamino]-ethyl}-phenyl)-benzenesulphonamide, 0.055 g (0.100 mmol) 1,1'-bis-(diphenylphosphino)-ferrocene, 0.022 g (0.100 mmol) palladium (II)acetate and 5 mL methanol were shaken in an autoclave under a carbon monoxide atmosphere of 2 bar for 15 h at 50° C. The reaction mixture was filtered and the filtrate was freed from solvent using the rotary evaporator. The residue was purified by flash column chromatography [methylene chloride/methanol (100:0→80:20)]. 0.480 g (0.986 mmol, 99%) methyl 1-{3-[2-(3-benzenesulphonylamino-phenyl)-2-hydroxy-ethylamino]-3-methyl-butyl}-1H-imidazole-4-carboxylate were obtained as a colourless solid.

Synthesis of 1-{3-[2-(3-benzenesulphonylamino-phenyl)-2-hydroxy-ethylamino]-3-methyl-butyl}-1H-imidazole-4-carboxylic acid

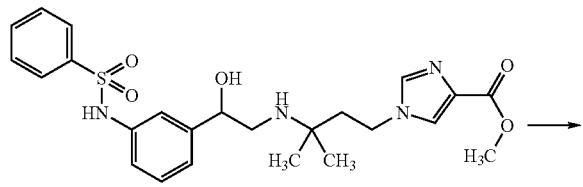

4.00 mL sodium hydroxide solution (1M) was added to 7.81 g (23.3 mmol) methyl 1-{3-[2-(3-benzenesulphonylamino-phenyl)-2-hydroxy-ethylamino]-3-methyl-butyl}-1H-imidazole-4-carboxylate in 8 mL tetrahydrofuran and stirred for 4 h at ambient temperature. The solvent was eliminated from the reaction mixture using the rotary evaporator and the residue was combined three times with 20 mL methanol and filtered. The combined methanolic phases were freed from solvent using the rotary evaporator and 0.390 g (0.825 mmol, 98%) 1-{3-[2-(3-benzenesulphonylamino-phenyl)-2-hydroxy-ethylamino]-3-methyl-butyl}-1H-imidazole-4-carboxylic acid were obtained as a colourless solid.

Example 5

Synthesis of tert-butyl {3-[3-(4-fluoro-phenyl)-2-oxo-imidazolidin-1-yl]-1,1-dimethyl-propyl}-carbamate

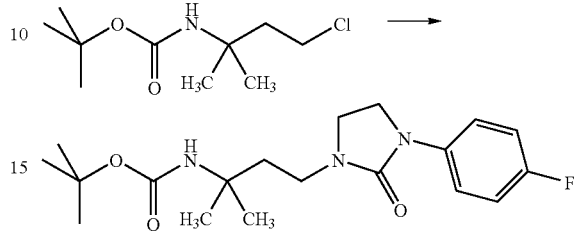

0.73 g (60% in oil, 18.3 mmol) sodium hydride were added batchwise to a solution of 3.69 g (16.6 mmol) 1-(4-fluoro-phenyl)-imidazolidin-2-one in 20 mL 1,3-dimethyl-3,4,5,6-tetrahydro-2(1H)-pyrimidone at 5° C. with vigorous stirring. After the development of gas had ended the reaction was stirred for 1 h at 0° C. and 3.00 g (16.6 mmol) tert-butyl (3-chloro-1,1-dimethyl-propyl)-carbamate and 0.62 g (1.67 mmol) tetrabutylammonium iodide were added. The reaction mixture was stirred for 48 h at ambient temperature and then poured into 500 mL ice water/ethyl acetate 2:1. The phases were separated and the aqueous phase was extracted three times with 150 mL ethyl acetate. The combined organic phases were washed five times with 150 mL water, then once with 150 mL saturated, aqueous sodium chloride solution, dried over sodium sulphate and the solvent was eliminated using the rotary evaporator. The residue was purified by flash column chromatography [petroleum ether/ethyl acetate (70:30)]. 1.35 g (3.69 mmol, 22%) tert-butyl [{3-[3-(4-fluoro-phenyl)-2-oxo-imidazolidin-1-yl]-1,1-dimethyl-propyl}-carbamate were obtained as a colourless solid.

Synthesis of 1-(3-amino-3-methyl-butyl)-3-(4-fluoro-phenyl)-imidazolidin-2-one

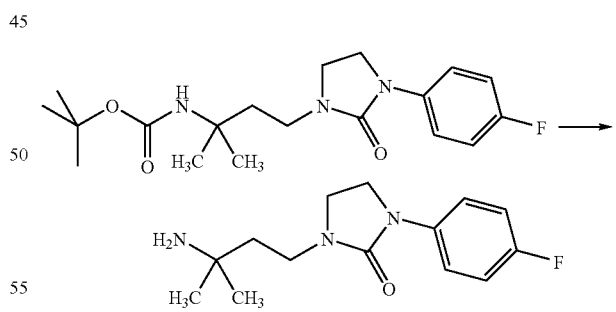

10 mL (130 mmol) trifluoroacetic acid were added to a solution of 1.35 g (3.9 mmol) tert-butyl {3-[3-(4-fluoro-phenyl)-2-oxo-imidazolidin-1-yl]-1,1-dimethyl-propyl}-carbamate in 20 mL dichloromethane at ambient temperature with vigorous stirring. The reaction mixture was stirred for 16 h at ambient temperature and the solvent was eliminated using the rotary evaporator. The residue was stirred with diethyl ether. 1.37 g (4.91 mmol, 98%) 1-(3-amino-3-methyl-butyl)-3-(4-fluoro-phenyl)-imidazolidin-2-one bistrifluoroacetate were obtained as a colourless solid.

Synthesis of N-[3-(2-{3-[3-(4-fluoro-phenyl)-2-oxo-imidazolidin-1-yl]-1,1-dimethyl-propylamino}-1-hydroxy-ethyl)-phenyl]-benzenesulphonamide

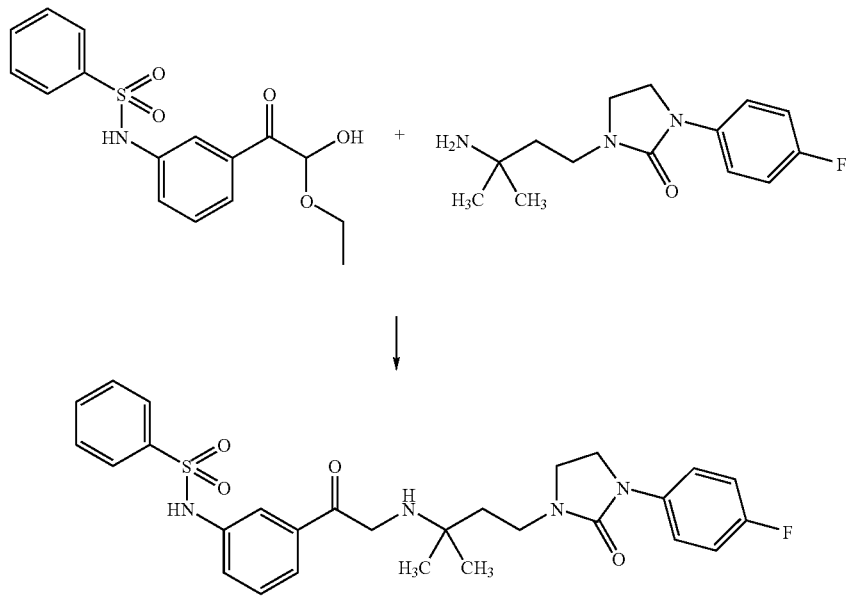

The free base was prepared from 0.34 g (0.90 mmol) 1-(3-amino-3-methyl-butyl)-3-(4-fluoro-phenyl)-imidazolidin-2-one bistrifluoroacetate by known methods. It was dissolved in 4 mL ethanol, combined with 0.20 g (0.60 mmol) N-[3-(2-ethoxy-2-hydroxy-acetyl)-phenyl]-benzenesulphonamide and refluxed for 15 h. The reaction mixture was cooled to 0° C. and then combined with 0.34 g (9.00 mmol) sodium borohydride. It was stirred for a further 24 h at ambient temperature and then combined with 20 mL saturated aqueous potassium carbonate solution. The aqueous phase was separated from the organic phase and extracted twice with 50 mL ethyl acetate. The combined organic phases were washed with 20 mL saturated aqueous sodium chloride solution, dried over magnesium sulphate and freed from the solvent using the rotary evaporator. The residue was purified by flash column chromatography [methylene chloride/methanol (98:2→75:25)]. 0.10 g (0.19 mmol, 31%) N-[3-(2-{3-[3-(4-fluoro-phenyl)-2-oxo-imidazolidin-1-yl]-1,1-dimethyl-propylamino}-1-hydroxy-ethyl)-phenyl]-benzenesulphonamide were obtained as a colourless solid.

Examples 1, 2, 3, 6, 7, 13, 15, 18, 24, 25, 29, 30, 31 and 37 were synthesised analogously to the method described in Example 5. The following reagents were used in the first reaction step instead of 1-(4-fluoro-phenyl)-imidazolidin-2-one:

Example 1

4-phenylimidazole

Example 2

2-methyl-2,3-dihydro-phthalazine-1,4-dione

Example 3

4-phenylimidazolidin-2-one

Example 6

4-(4-methoxyphenyl)imidazole

Example 7

4-(imidazol-4-yl)-phenol

Example 13

1-pyridin-2-yl-imidazolidin-2-one

Example 15

4-(imidazol-4-yl)-pyridine

Example 18

1-(4-hydroxyphenyl)-imidazolidin-2-one

Example 24

5-nitrobenzimidazole

Example 25

4-(4-methoxyphenyl) [1,2,3]triazole

Example 29

4-(4-methoxyphenyl)-imidazolidin-2-one

Example 30

4-(4-nitrophenyl)-imidazolidin-2-one

Example 31

3-(4-methoxyphenyl) [1,2,4]triazole

Example 37 ethyl benzimidazole-5-carboxylate

Synthesis of 3-[4-(4-hydroxy-phenyl)-imidazol-1-yl]-1,1-dimethyl-propylamine (the Amine Component for the Last Step of the Synthesis of Example 7)

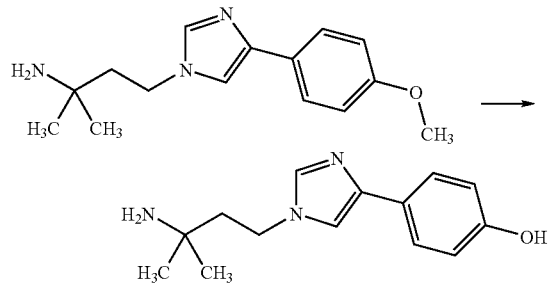

1.0 g (4.00 mmol) 3-[4-(4-methoxy-phenyl)-imidazol-1-yl]-1,1-dimethyl-propylamine and 4.00 g pyridine hydrochloride were stirred for 2 h at 200° C. in a sealed reaction vessel in a microwave. The reaction mixture was poured into 40 mL ice water and 40 mL ethyl acetate, the pH of the aqueous phase was adjusted to over 9 with sodium hydroxide solution (2M) and the phases were separated. The aqueous phase was extracted five times with 50 mL ethyl acetate. The combined organic phases were dried over magnesium sulphate and the solvent was eliminated using the rotary evaporator. 0.530 g (2.16 mmol, 54%) 3-[4-(4-hydroxy-phenyl)-imidazol-1-yl]-1,1-dimethyl-propylamine were obtained as a colourless solid.

1-(3-amino-3-methyl-butyl)-3-(4-hydroxy-phenyl)-imidazolidin-2-one (amine component for the last step of the synthesis of Example 18) was synthesised from 1-(3-amino-3-methyl-butyl)-3-(4-methoxy-phenyl)-imidazolidin-2-one analogously to the synthesis of 3-[4-(4-hydroxy-phenyl)-imidazol-1-yl]-1,1-dimethyl-propylamine (amine component for the last step of the synthesis of Example 7).

1-(3-Amino-3-methyl-butyl)-3-pyridin-2-yl-imidazolidin-2-one (amine component for the last step of the synthesis of Example 13) was synthesised analogously to the procedures laid down in DE2548663 and DE2528078.

Example 8

Synthesis of N-[3-(2-{3-[4-(4-amino-phenyl)-imidazol-1-yl]-1,1-dimethyl-propylamino}-1-hydroxy-ethyl)-phenyl]-benzenesulphonamide

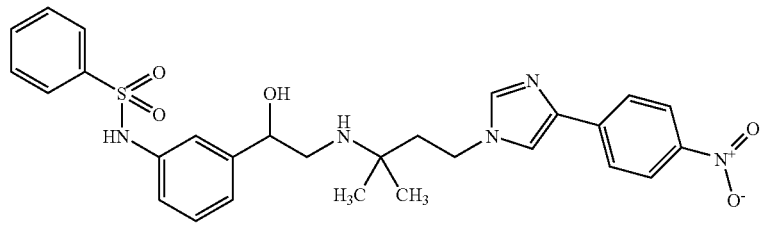

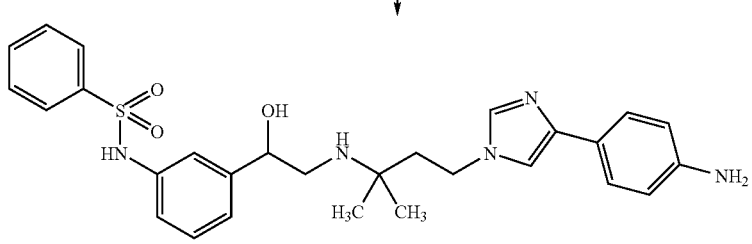

1.69 g (3.07 mmol) N-[3-(2-{3-[4-(4-nitro-phenyl)-imidazol-1-yl]-1,1-dimethyl-propylamino}-1-hydroxyethyl)-phenyl]-benzenesulphonamide, 0.10 g palladium on activated charcoal, and 30 mL methanol were shaken in an autoclave at ambient temperature under a hydrogen atmosphere of 1 bar for 3 h. The reaction mixture was filtered and the filtrate was freed from solvent using the rotary evaporator. 1.59 g (3.05 mmol, 99%) N-[3-(2-{3-[4-(4-amino-phenyl)-imidazol-1-yl]-1,1-dimethyl-propylamino}-1-hydroxyethyl)-phenyl]-benzenesulphonamide were obtained as a colourless solid.

Examples 17, 32, 34 and 35 were synthesised analogously to the method described in Example 8. The following compounds were used instead of N-[3-(2-{3-[4-(4-nitro-phenyl)-imidazol-1-yl]-1,1-dimethyl-propylamino}-1-hydroxy-ethyl)-phenyl]-benzenesulphonamide:

Example 17 benzyl 4-(1-{3-[2-(3-benzenesulphonylamino-phenyl)-2-hydroxy-ethylamino]-3-methyl-butyl}-1H-imidazol-4-yl)-benzoate (Example 16)

Example 32

N-[3-(2-{1,1-dimethyl-3-[3-(4-nitro-phenyl)-2-oxo-imidazolidin-1-yl]-propylamino}-1-hydroxy-ethyl)-phenyl]-benzenesulphonamide (Example 30)

Example 34

N-[3-(2-{3-[4-(3,5-dimethyl-isoxazol-4-yl)-imidazol-1-yl]-1,1-dimethyl-propylamino}-1-hydroxy-ethyl)-phenyl]-benzenesulphonamide (Example 20)

Example 35

N-[3-(2-{1,1-dimethyl-3-[4-(4-nitro-phenyl)-imidazol-1-yl]-propylamino}-1-hydroxy-ethyl)-phenyl]-benzenesulphonamide (Example 4)

Example 12

Synthesis of N-[3-(1-hydroxy-2-{3-[4-(4-N,N-dimethylsulphamylamino-phenyl)-imidazol-1yl]-1,1-dimethyl-propylamino}-ethyl)-phenyl]-benzenesulphonamide

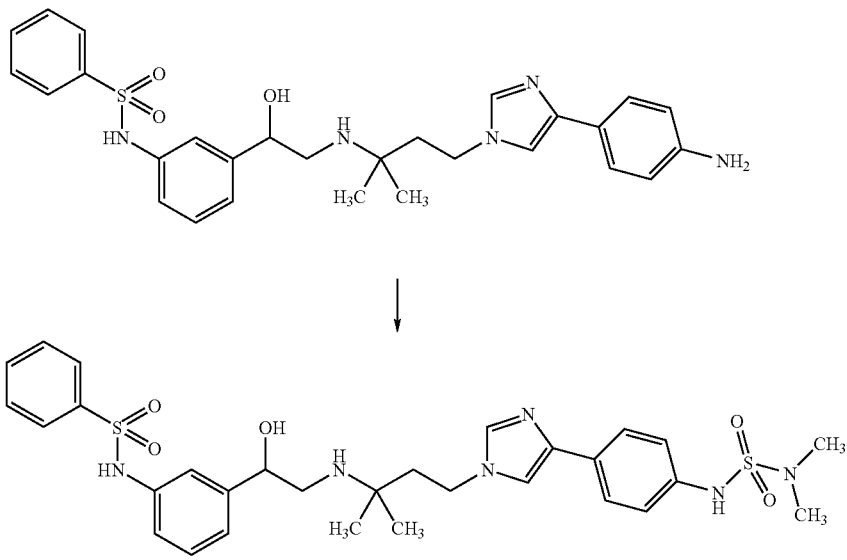

0.064 mL (0.600 mmol) N,N-dimethylsulphamoyl chloride was added at 0° C. to 0.208 g (0.400 mmol) N-[3-(2-{3-[4-(4-amino-phenyl)-imidazol-1-yl]-1,1-dimethyl-propylamino}-1-hydroxyethyl)-phenyl]-benzenesulphonamide in 4 mL pyridine and the mixture was stirred for 16 h at ambient temperature. The reaction mixture was poured into 50 ml hydrochloric acid (1M)/ethyl acetate 1:1. The phases were separated and the aqueous phase was extracted three times with 20 mL ethyl acetate. The combined organic phases were dried over sodium sulphate and the solvent was eliminated using the rotary evaporator. The residue was purified by flash column chromatography [methylene chloride/methanol (100:0→70:30)], and 0.131 g (0.209 mmol, 52%) N-[3-(1-hydroxy-2-{3-[4-(4-N,N-dimethylsulphamylamino-phenyl)-imidazol-1-yl]-1,1-dimethyl-propylamino}-ethyl)-phenyl]-benzenesulphonamide were obtained as a colourless solid.

The compounds of formula (IA) listed in Table 1 were obtained, inter alia, analogously to the method described above.

The abbreviation $X_2$ used in Table 1 denotes a link to the position in the general formula shown in Table 1 instead of the corresponding groups $R^2$.

TABLE 1

| Example | $R^2$ | $R_f$ value | MS |
|---|---|---|---|
| 1 | imidazole-phenyl ($X_2$-N-imidazole with phenyl) | DCM/MeOH 85/15; $R_f$ 0.52 | ESI $(M + H)^+ = 505$ |
| 2 | 2-methyl-phthalazine-1,4-dione ($X_2$ linked) | DCM/MeOH/NH$_4$OH 90/10/1; $R_f$ 0.50 | ESI $(M + H)^+ = 537$ |

TABLE 1-continued

| Example | R² | R_f value | MS |
|---|---|---|---|
| 3 | (1-phenyl-imidazolidin-2-one-3-yl) | DCM/MeOH/NH₄OH 90/10/1; R_f 0.48 | ESI (M + H)⁺ = 523 |
| 4 | (4-(4-nitrophenyl)imidazol-1-yl) | DCM/MeOH/NH₄OH 90/10/1; R_f 0.38 | ESI (M + H)⁺ = 550 |
| 5 | (1-(4-fluorophenyl)imidazolidin-2-one-3-yl) | DCM/MeOH/NH₄OH 90/10/1; R_f 0.39 | ESI (M + H)⁺ = 539 |
| 6 | (4-(4-methoxyphenyl)imidazol-1-yl) | DCM/MeOH/NH₄OH 90/10/1; R_f 0.36 | ESI (M + H)⁺ = 535 |
| 7 | (4-(4-hydroxyphenyl)imidazol-1-yl) | DCM/MeOH/NH₄OH 90/10/1; R_f 0.30 | ESI (M + H)⁺ = 521 |
| 8 | (4-(4-aminophenyl)imidazol-1-yl) | DCM/MeOH/NH₄OH 90/10/1; R_f 0.32 | ESI (M + H)⁺ = 520 |
| 9 | (4-(4-methanesulfonylaminophenyl)imidazol-1-yl) | DCM/MeOH/NH₄OH 90/10/1; R_f 0.23 | ESI (M + H)⁺ = 598 |
| 10 | (4-iodo-imidazol-1-yl) | DCM/MeOH/NH₄OH 90/10/1; R_f 0.34 | ESI (M + H)⁺ = 555 |
| 11 | (4-methoxycarbonyl-imidazol-1-yl) | DCM/MeOH 90/10; R_f 0.20 | ESI (M + H)⁺ = 487 |

TABLE 1-continued

| Example | R² | R_f value | MS |
|---------|-----|-----------|-----|
| 12 | imidazole-X₂, phenyl-NH-S(O)₂-N(CH₃)₂ | DCM/MeOH 90/10; R_f 0.26 | ESI (M + H)⁺ = 627 |
| 13 | imidazolidinone-X₂, N-(2-pyridyl) | DCM/MeOH 90/10; R_f 0.26 | ESI (M + H)⁺ = 524 |
| 14 | imidazole-X₂, COOH | DCM/MeOH/AcOH 70/30/3; R_f 0.07 | ESI (M + H)⁺ = 473 |
| 15 | imidazole-X₂, 4-pyridyl | DCM/MeOH/NH₄OH 90/10/1; R_f 0.25 | ESI (M + H)⁺ = 506 |
| 16 | imidazole-X₂, phenyl-C(O)O-CH₂-phenyl | DCM/MeOH/NH₄OH 90/10/1; R_f 0.34 | ESI (M + H)⁺ = 639 |
| 17 | imidazole-X₂, phenyl-COOH | DCM/MeOH/AcOH 70/30/3; R_f 0.57 | ESI (M + H)⁺ = 549 |
| 18 | imidazolidinone-X₂, N-(4-hydroxyphenyl) | DCM/MeOH/NH₄OH 90/10/1; R_f 0.34 | ESI (M + H)⁺ = 539 |
| 19 | imidazole-X₂, phenyl-NH-C(O)-CH₃ | DCM/MeOH/NH₄OH 90/10/1; R_f 0.21 | ESI (M + H)⁺ = 562 |
| 20 | imidazole-X₂, 3,5-dimethylisoxazol-4-yl | DCM/MeOH/NH₄OH 90/10/1; R_f 0.21 | ESI (M + H)⁺ = 524 |

TABLE 1-continued

| Example | R² | R_f value | MS |
|---|---|---|---|
| 21 | imidazole-CH=C(N)-pyridine-OCH₃ | DCM/MeOH/NH₄OH 90/10/1; R_f 0.31 | ESI (M + H)⁺ = 536 |
| 22 | imidazole-thiophene-CH₃ | DCM/MeOH/NH₄OH 90/10/1; R_f 0.36 | ESI (M + H)⁺ = 525 |
| 23 | imidazole-C₆H₄-F | DCM/MeOH 90/10; R_f 0.29 | ESI (M + H)⁺ = 523 |
| 24 | benzimidazole-NO₂ | DCM/MeOH 90/10; R_f 0.29 | ESI (M + H)⁺ = 524 |
| 25 | triazole-C₆H₄-OCH₃ | DCM/MeOH 90/10; R_f 0.23 | ESI (M + H)⁺ = 536 |
| 26 | imidazole-thiophene | DCM/MeOH/NH₄OH 90/10/1; R_f 0.36 | ESI (M + H)⁺ = 511 |
| 27 | imidazole-C₆H₄-N(CH₃)₂ | DCM/MeOH/NH₄OH 90/10/1; R_f 0.32 | ESI (M + H)⁺ = 548 |
| 28 | imidazole-C₆H₄-C(O)OCH₂CH₃ | DCM/MeOH/NH₄OH 90/10/1; R_f 0.32 | ESI (M + H)⁺ = 577 |
| 29 | imidazolidinone-C₆H₄-OCH₃ | DCM/MeOH/NH₄OH 90/10/1; R_f 0.46 | ESI (M + H)⁺ = 553 |

TABLE 1-continued
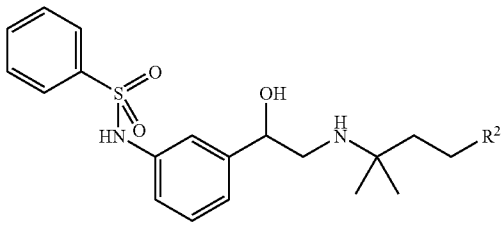
| Example | R² | R_f value | MS |
|---|---|---|---|
| 30 | 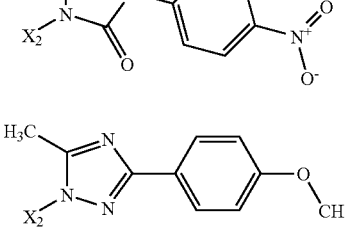 | DCM/MeOH/NH₄OH 90/10/1; R_f 0.42 | ESI (M + H)⁺ = 568 |
| 31 | 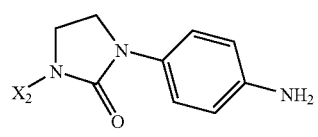 | DCM/MeOH 90/10; R_f 0.21 | ESI (M + H)⁺ = 550 |
| 32 | 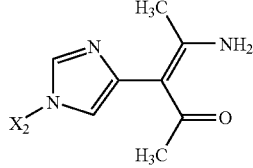 | DCM/MeOH/NH₄OH 90/10/1; R_f 0.33 | ESI (M + H)⁺ = 538 |
| 33 | 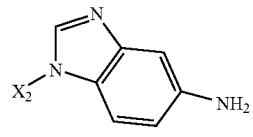 | RP-18 F 254 MeCN/H₂O/AcOH 20/80/1; R_f 0.33 | ESI (M + H)⁺ = 526 |
| 34 | 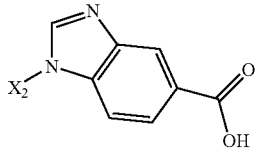 | DCM/MeOH/NH₄OH 90/9/1; R_f 0.27 | ESI (M + H)⁺ = 494 |
| 35 | 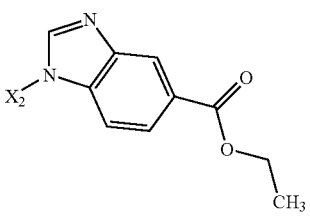 | DCM/MeOH/AcOH 80/20/2; R_f 0.50 | ESI (M + H)⁺ = 523 |
| 36 | 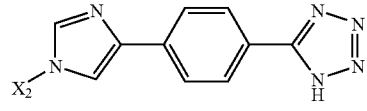 | DCM/MeOH/NH₄OH 90/9/1; R_f 0.35 | ESI (M + H)⁺ = 551 |
| 37 |  | RP-18 F 254 MeCN/H₂O 1/1; R_f 0.59 | ESI (M + H)⁺ = 573 |

TABLE 1-continued

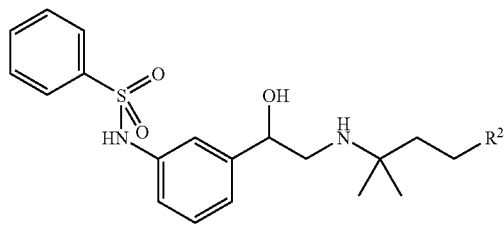

| Example | R² | R_f-value | MS |
|---|---|---|---|
| 38 | ![structure with imidazole, phenyl, C(=O)NHOH, X₂] | RP-18 F 254 MeCN/H₂O/AcOH 250/250/1; R_f 0.51 | ESI (M + H)⁺ = 564 |

Abbreviations:
AcOH: glacial acetic acid
DCM: dichloromethane
MeCN acetonitrile
MeOH: methanol
NH₄OH: conc. solution of ammonia in water
RP-18 F254: Merck reversed phase silica gel 18 F254 TLC plate Unless otherwise stated, all the $R_f$ values were determined on Merck silica gel 60 F254 TLC plates.

Chemical names of the Examples (Example Nos. correspond to the numbering used below):

1) N-(3-{2-[1,1-dimethyl-3-(4-phenyl-imidazol-1-yl)-propylamino]-1-hydroxy-ethyl}-phenyl)-benzenesulphonamide
2) N-(3-{2-[1,1-dimethyl-3-(3-methyl-1,4-dioxo-3,4-dihydro-1H-phthalazin-2-yl)-propylamino]-1-hydroxy-ethyl}-phenyl)-benzenesulphonamide
3) N-(3-{2-[1,1-dimethyl-3-(2-oxo-3-phenyl-imidazolidin-1-yl)-propylamino]-1-hydroxy-ethyl}-phenyl)-benzenesulphonamide
4) N-[3-(2-{1,1-dimethyl-3-[4-(4-nitro-phenyl)-imidazol-1-yl]-propylamino}-1-hydroxy-ethyl)-phenyl]-benzenesulphonamide
5) N-[3-(2-{3-[3-(4-fluoro-phenyl)-2-oxo-imidazolidin-1-yl]-1,1-dimethyl-propylamino}-1-hydroxy-ethyl)-phenyl]-benzenesulphonamide
6) N-[3-(1-hydroxy-2-{3-[4-(4-methoxy-phenyl)-imidazol-1-yl]-1,1-dimethyl-propylamino}-ethyl)-phenyl]-benzenesulphonamide
7) N-[3-(1-hydroxy-2-{3-[4-(4-hydroxy-phenyl)-imidazol-1-yl]-1,1-dimethyl-propylamino}-ethyl)-phenyl]-benzenesulphonamide
8) N-[3-(2-{3-[4-(4-amino-phenyl)-imidazol-1-yl]-1,1-dimethyl-propylamino}-1-hydroxy-ethyl)-phenyl]-benzenesulphonamide
9) N-[3-(1-hydroxy-2-{3-[4-(4-methanesulphonylamino-phenyl)-imidazol-1-yl]-1,1-dimethyl-propylamino}-ethyl)-phenyl]-benzenesulphonamide
10) N-(3-{1-hydroxy-2-[3-(4-iodo-imidazol-1-yl)-1,1-dimethyl-propylamino]-ethyl}-phenyl)-benzenesulphonamide
11) methyl 1-{3-[2-(3-benzenesulphonylamino-phenyl)-2-hydroxy-ethylamino]-3-methyl-butyl}-1H-imidazole-4-carboxylate
12) N-[3-(1-hydroxy-2-{3-[4-(4-N,N-dimethyl-sulphamoylamino-phenyl)-imidazol-1-yl]-1,1-dimethyl-propylamino}-ethyl)-phenyl]-benzenesulphonamide
13) N-(3-{2-[1,1-dimethyl-3-(2-oxo-3-pyridin-2-yl-imidazolidin-1-yl)-propylamino]-1-hydroxy-ethyl}-phenyl)-benzenesulphonamide
14) 1-{3-[2-(3-benzenesulphonylamino-phenyl)-2-hydroxy-ethylamino]-3-methyl-butyl}-1H-imidazole-4-carboxylic acid
15) N-(3-{2-[1,1-dimethyl-3-(4-pyridin-4-yl-imidazol-1-yl)-propylamino]-1-hydroxy-ethyl}-phenyl)-benzenesulphonamide
16) benzyl 4-(1-{3-[2-(3-benzenesulphonylamino-phenyl)-2-hydroxy-ethylamino]-3-methyl-butyl}-1H-imidazol-4-yl)-benzoate
17) 4-(1-{3-[2-(3-benzenesulphonylamino-phenyl)-2-hydroxy-ethylamino]-3-methyl-butyl}-1H-imidazol-4-yl)-benzoic acid
18) N-[3-(1-hydroxy-2-{3-[3-(4-hydroxy-phenyl)-2-oxo-imidazolidin-1-yl]-1,1-dimethyl-propylamino}-ethyl)-phenyl]-benzenesulphonamide
19) N-[4-(1-{3-[2-(3-benzenesulphonylamino-phenyl)-2-hydroxy-ethylamino]-3-methyl-butyl}-1H-imidazol-4-yl)-phenyl]-acetamide
20) N-[3-(2-{3-[4-(3,5-dimethyl-isoxazol-4-yl)-imidazol-1-yl]-1,1-dimethyl-propylamino}-1-hydroxy-ethyl)-phenyl]-benzenesulphonamide
21) N-[3-(1-hydroxy-2-{3-[4-(6-methoxy-pyridin-3-yl)-imidazol-1-yl]-1,1-dimethyl-propylamino}-ethyl)-phenyl]-benzenesulphonamide
22) N-[3-(2-{1,1-dimethyl-3-[4-(5-methyl-thiophen-2-yl)-imidazol-1-yl]-propylamino}-1-hydroxy-ethyl)-phenyl]-benzenesulphonamide
23) N-[3-(2-{3-[4-(4-fluoro-phenyl)-imidazol-1-yl]-1,1-dimethyl-propylamino}-1-hydroxy-ethyl)-phenyl]-benzenesulphonamide
24) N-(3-{2-[1,1-dimethyl-3-(5-nitro-benzoimidazol-1-yl)-propylamino]-1-hydroxy-ethyl}-phenyl)-benzenesulphonamide
25) N-[3-(1-hydroxy-2-{3-[4-(4-methoxy-phenyl)-[1.2.3]triazol-1-yl]-1,1-dimethyl-propylamino}-ethyl)-phenyl]-benzenesulphonamide
26) N-(3-{2-[1,1-dimethyl-3-(4-thiophen-2-yl-imidazol-1-yl)-propylamino]-1-hydroxy-ethyl}-phenyl)-benzenesulphonamide 27) N-[3-(2-{3-[4-(4-dimethylamino-phenyl)-imidazol-1-yl]-1,1-dimethyl-propylamino}-1-hydroxy-ethyl)-phenyl]-benzenesulphonamide
28) ethyl 4-(1-{3-[2-(3-benzenesulphonylamino-phenyl)-2-hydroxy-ethylamino]-3-methyl-butyl}-1H-imidazol-4-yl)-benzoate
29) N-[3-(1-hydroxy-2-{3-[3-(4-methoxy-phenyl)-2-oxo-imidazolidin-1-yl]-1,1-dimethyl-propylamino}-ethyl)-phenyl]-benzenesulphonamide
30) N-[3-(2-{1,1-dimethyl-3-[3-(4-nitro-phenyl)-2-oxo-imidazolidin-1-yl]-propylamino}-1-hydroxy-ethyl)-phenyl]-benzenesulphonamide
31) N-[3-(1-hydroxy-2-{3-[3-(4-methoxy-phenyl)-5-methyl-[1,2,4]triazol-1-yl]-1,1-dimethyl-propylamino}-ethyl)-phenyl]-benzenesulphonamide
32) N-[3-(2-{3-[3-(4-amino-phenyl)-2-oxo-imidazolidin-1-yl]-1,1-dimethyl-propyl-amino}-1-hydroxy-ethyl)-phenyl]-benzenesulphonamide
33) N-[3-(2-{3-[4-(1-acetyl-2-amino-propenyl)-imidazol-1-yl]-1,1-dimethyl-propylamino}-1-hydroxy-ethyl)-phenyl]-benzenesulphonamide
34) N-(3-{2-[3-(5-amino-benzoimidazol-1-yl)-1,1-dimethyl-propylamino]-1-hydroxy-ethyl}-phenyl)-benzenesulphonamide
35) 1-{3-[2-(3-benzenesulphonylamino-phenyl)-2-hydroxy-ethylamino]-3-methyl-butyl}-1H-benzoimidazole-5-carboxylic acid
36) ethyl 1-{3-[2-(3-benzenesulphonylamino-phenyl)-2-hydroxy-ethylamino]-3-methyl-butyl}-1H-benzoimidazole-5-carboxylate
37) N-{3-[2-(1,1-dimethyl-3-{4-[4-(1H-tetrazol-5-yl)-phenyl]-imidazol-1-yl}-propylamino)-1-hydroxy-ethyl]-phenyl}-benzenesulphonamide
38) 4-(1-{3-[2-(3-benzenesulphonylamino-phenyl)-2-hydroxy-ethylamino]-3-methyl-butyl}-1H-imidazol-4-yl)-N-hydroxy-benzamide The (R)- and (S)-enantiomers of the Examples may be obtained from the racemate by chiral HPLC, for example (e.g. column: Chirobiotic T, 250×4.6 mm obtained from Messrs Astec). The mobile phase used may be methanol with 0.05% triethylamine and 0.05% acetic acid (eluant A) in acetonitrile. Silica gel with a particle size of 5 μm to which the glycoprotein teicoplanin is covalently bound may be used as the column material. Of outstanding importance according to the invention are the (R)-enantiomers of general formula:

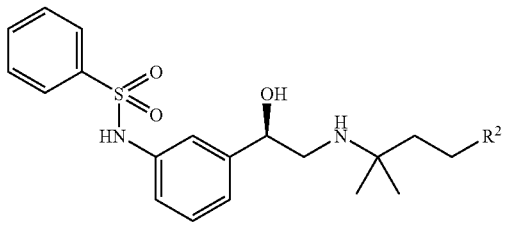

The following enantiomers were obtained, for example:

Example 4

30% Eluant A in Acetonitrile retention time [(R)—N-[3-(2-{1,1-dimethyl-3-[4-(4-nitro-phenyl)-imidazol-1-yl]-propylamino}-1-hydroxy-ethyl)-phenyl]-benzenesulphonamide]=25.5 min
retention time [(S)—N-[3-(2-{1,1-dimethyl-3-[4-(4-nitro-phenyl)-imidazol-1-yl]-propylamino}-1-hydroxy-ethyl)-phenyl]-benzenesulphonamide]=30.0 min.

Example 8

30% Eluant A in Acetonitrile retention time [(R)—N-[3-(2-{3-[4-(4-amino-phenyl)-imidazol-1-yl]-1,1-dimethyl-propylamino}-1-hydroxy-ethyl)-phenyl]-benzenesulphonamide]=22.4 min,
retention time [(S)—N-[3-(2-{3-[4-(4-amino-phenyl)-imidazol-1-yl]-1,1-dimethyl-propylamino}-1-hydroxy-ethyl)-phenyl]-benzenesulphonamide]=25.1 min.

Example 17

30% Eluant A in Acetonitrile retention time [(R)-4-(1-{3-[2-(3-benzenesulphonylamino-phenyl)-2-hydroxy-ethylamino]-3-methyl-butyl}-1H-imidazol-4-yl)-benzoic acid]=11.4 min,
retention time [(S)-4-(1-{3-[2-(3-benzenesulphonylamino-phenyl)-2-hydroxy-ethylamino]-3-methyl-butyl}-1H-imidazol-4-yl)-benzoic acid]=12.9 min.

Example 28

50% Eluant A in Acetonitrile retention time ethyl [(R)-4-(1-{3-[2-(3-benzenesulphonylamino-phenyl)-2-hydroxy-ethylamino]-3-methyl-butyl}-1H-imidazol-4-yl)-benzoate]=13.2 min,
retention time ethyl [(S)-4-(1-{3-[2-(3-benzenesulphonylamino-phenyl)-2-hydroxy-ethylamino]-3-methyl-butyl}-1H-imidazol-4-yl)-benzoate]=14.6 min.

As has been found, the compounds of general formula (I) are characterised by their great versatility in the therapeutic field. Particular mention should be made of those applications in which the effects of beta-3-agonists, particularly selective beta-3-agonists play a part.

Such diseases include for example:
atherosclerosis, cholangitis, gall bladder disease, chronic cystitis, chronic bladder inflammation; chronic prostatitis, cystospasm, depression, duodenal ulcer, duodenitis, dysmenorrhoea; increased intraocular pressure and glaucoma, enteritis, oesophagitis, gastric ulcer, gastritis, gastrointestinal disorders caused by contraction(s) of the smooth muscle, gastrointestinal disorders incl. gastric ulcer; gastrointestinal ulceration, gastrointestinal ulcers, glaucoma, glucosuria, hyperanakinesia, hypercholesterolaemia, hyperglycaemia, hyperlipaemia, arterial hypertension, hypertriglyceridaemia, insulin resistance, intestinal ulceration or small bowel ulcers (incl. inflammatory bowel diseases, ulcerative colitis, Crohn's disease and proctitis=inflammation of the rectum), irritable colon and other diseases with decreased intestinal motility, depression, melancholy, pollacisuria, frequent urinary urgency, nervous neurogenic inflammation, neurogenic bladder dysfunction, neurogenic inflammation of the respiratory tract, neuropathic bladder dysfunction, nycturia, non-specific diarrhoea, dumping syndrome, obesity, fatness, pancreatitis, inflammation of the pancreas, stomach ulcers, prostate diseases such as benign prostatic hyperplasia, enlarged prostate, spasm, cramp, type 2 diabetes mellitus, irritable bladder or concrement of the lower urinary tract.

The beta-3 agonists according to the invention are particularly suitable for the treatment of obesity, insulin resistance, type 2 diabetes mellitus, urinary incontinence, irritable colon and other diseases with decreased intestinal motility or depression, particularly for the treatment of diabetes and obesity.

The activity of the beta-3 agonists can be determined for example in a lipolysis test. The test procedure may be carried out as follows:

Adipocytes were isolated from fatty tissue ex vivo by modifying a method according to Rodbell (Rodbell, M. Metabolism of isolated fat cells. I. Effects of hormones on glucose metabolism and lipolysis. *J Biol Chem* 239: 375-380.1964). The excised fatty tissue was cut into small pieces and mixed with 1 mg/ml collagenase in Krebs Ringer Buffer (KRB) containing 6 mM glucose and 2% albumin by gently shaking for 30-40 min at 37° C. The cells were filtered through a gauze, washed twice with KRB and in each case 50-150 g were centrifuged for 5 min. 10 µl of the centrifuged adipocytes were incubated with 90 µl of a compound according to the invention (agonist) at concentrations of between $10^{-15}$ to $10^{-4}$ M. The agonists were incubated over 40 min at 37° C. A varying release of glycerol in the medium indicated that the fat cell lipolysis had altered as a result of the addition of the agonist. Released glycerol was detected enzymatically with a Sigma kit (triglyceride (GPO Trinder) Reagent A; Cat. #337-40A), as described below.

Glycerol is phosphorylated by ATP via glycerol kinase. The resulting glycerol-1-phosphate is oxidised by glycerol-phosphate oxidase to form dihydroxyacetone phosphate and hydrogen peroxide. Then a quinonimine dye is produced by the peroxidase-catalysed coupling of sodium-N-ethyl-N-(3-sulphopropyl)m-ansidine and 4-aminoantipyrine. The dye has an absorption peak at 540 nm. The absorption is directly proportional to the glycerol concentration in the samples.

The new compounds may be used for the prevention or short-term or long-term treatment of the above-mentioned diseases, and may also be used in conjunction with other active substances used for the same indications. These include, for example, antidiabetics, such as metformin, sulphonylureas (e.g. glibenclamid, tolbutamide, glimepiride), nateglinide, repaglinide, thiazolidinedione (e.g. rosiglitazone, pioglitazone), PPAR-gamma agonists (e.g. GI 262570), alpha-gluco-sidase inhibitors (e.g. acarbose, voglibose), alpha2 antagonists, insulin and insulin analogues, GLP-1 and GLP-1 analogues (e.g. exendin-4) or amylin. Also, inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, cholesterol absorption inhibitors such as for example ezetimibe, bile acid-binding substances such as for example cholestyramine, HDL-raising compounds such as for example inhibitors of CETP or regulators of ABC1 or active substances for the treatment of obesity, such as e.g. sibutramine or tetrahydrolipostatin.

In particular, they may also be combined with drugs for treating high blood pressure such as e.g. AII antagonists or ACE inhibitors, diuretics, β-blockers, and other modulators of the adrenergic system or combinations thereof. In addition, combinations with stimulators of the adrenergic system via alpha 1 and alpha 2 and also beta 1, beta 2 and beta 3 receptors are particularly suitable.

The compounds of general formula (I) may be used on their own or in conjunction with other active substances according to the invention, optionally also in conjunction with other pharmacologically active substances. Suitable preparations include for example tablets, capsules, suppositories, solutions, particularly solutions for injection (s.c., i.v., i.m.) and infusion, elixirs, emulsions or dispersible powders. The content of the pharmaceutically active compound(s) should be in the range from 0.1 to 90 wt. %, preferably 0.5 to 50 wt. % of the composition as a whole, i.e. in amounts which are sufficient to achieve the dosage range specified below. The specified doses may be taken several times a day, if necessary.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, optionally organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, preferably oral. For oral administration the tablets may, of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation Examples which follow illustrate the present invention without restricting its scope:

Examples of Pharmaceutical Formulations

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:

1. A compound of the formula

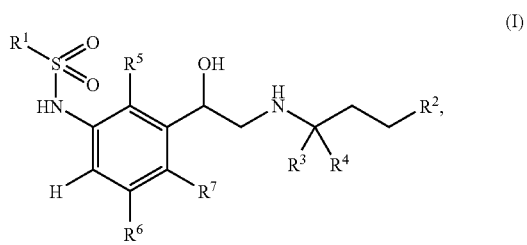

(I)

wherein $R^1$ denotes an optionally substituted aryl or heteroaryl group, $R^2$ denotes an optionally substituted heteroaryl or heterocyclyl group selected from

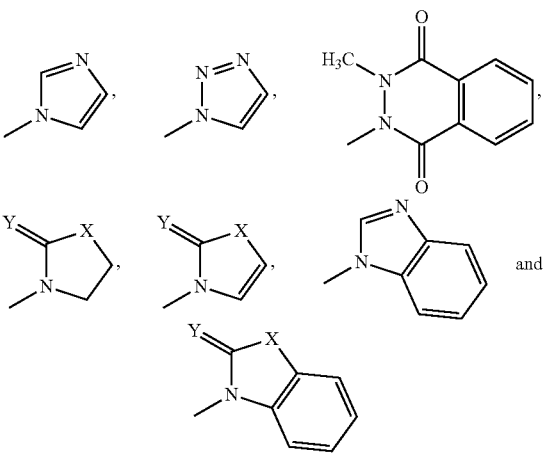

and wherein X denotes an —$NR^9$— group and

Y denotes an oxygen or sulphur atom, and $R^9$ denotes a hydrogen atom or a group selected from among $C_1$-$C_{10}$-alkyl, $C_3$-$C_8$-cycloalkyl, heterocyclyl, aryl or heteroaryl, while the groups mentioned for $R^9$ hereinbefore may each be substituted by one of the groups mentioned for $R^{10}$, $R^3$ and $R^4$ independently of one another denote a hydrogen atom or an optionally substituted group selected from among $C_1$-$C_5$-alkyl, $C_3$-$C_6$-cycloalkyl, heterocyclyl, aryl and heteroaryl, or $R^3$ and $R^4$ together represent a 2- to 7-membered alkylene bridge, $R^5$, $R^6$ and $R^7$ independently of one another denote a hydrogen atom or a group selected from among optionally substituted $C_1$-$C_{10}$-alkyl, alkenyl, alkynyl, $C_6$-$C_{10}$-aryl, heterocyclyl, $C_3$-$C_8$-cycloalkyl, —$NR^8$—$C_1$-$C_5$-alkyl, —$NR^8$-aryl, halogen, CN, —$NR^8CO$—($C_1$-$C_5$-alkyl), —$NR^8CO$-aryl, —$NR^8SO_2$—($C_1$-$C_5$-alkyl), —$NR^8SO_2$-aryl, —$CO_2R^8$, —$SO_2R^8$, —$CONHR^8$, —$SO_2NHR^8$ and —$OR^8$, while the above-mentioned alkyl groups may be substituted in each case, $R^8$ denotes a hydrogen atom or a $C_1$-$C_5$-alkyl group, and $R^{10}$ denotes OH, $NO_2$, CN, —$OCHF_2$, —$OCF_3$, —$NH_2$, —NH-alkyl, —N(-alkyl)-alkyl, —NH-aryl, —N(-alkyl)-aryl, —NHCO-alkyl, —NHCO$_2$-alkyl, —NHCO-aryl, —N(-alkyl)-CO-alkyl, —N(-alkyl)-CO-aryl, —NHSO$_2$-alkyl, —NHSO$_2$-aryl, —N(-alkyl)-SO$_2$-alkyl, —N(-alkyl)-SO$_2$-aryl, —CO$_2$-alkyl, —SO$_2$-alkyl, —SO$_2$-aryl, —CONH-alkyl, —CONH-aryl, —CON(-alkyl)-alkyl, —CON(-alkyl)-aryl, —SO$_2$NH-alkyl, —SO$_2$NH-aryl, —SO$_2$N(-alkyl)-alkyl, —SO$_2$N(-alkyl)-aryl, —O-alkyl, —O-aryl, —S-alkyl, —S-aryl, halogen, $C_1$-$C_{10}$-alkyl, —O—($C_1$-$C_3$-alkyl), —COOH, —CONH$_2$, —CON(-alkyl)-SO$_2$-alkyl, —CONHSO$_2$-alkyl, —CONHOH, 2,5-dihydro-5-oxo-4H-1,2,4-oxadiazol-3-yl, 2,5-dihydro-5-oxo-4H-1,2,4-thiadiazol-3-yl, 2,5-dihydro-2-oxo-3H-1,2,4,5-oxathiadiazol-4-yl, 1-acetyl-2-amino-propen-1-yl, tetrazolyl, heterocyclyl, aryl or heteroaryl, or a tautomer or pharmaceutically acceptable salt thereof.

2. A compound of the formula (I) according to claim 1, wherein $R^2$ to $R^7$ are defined as in claim 1, and $R^1$ denotes an optionally substituted phenyl group, or a tautomer or pharmaceutically acceptable salt thereof.

3. A compound of the formula (I) according to claim 1, wherein $R^1$ and $R^2$ may each be substituted by one or more groups $R^{10}$, or a tautomer or pharmaceutically acceptable salt thereof.

4. A compound of the formula I, according to claim 1, wherein $R^3$ and $R^4$ independently of one another represent a hydrogen atom or a methyl or ethyl group or $R^3$ and $R^4$ together represent a 2- to 5-membered alkylene bridge, or a tautomer or pharmaceutically acceptable salt thereof.

5. A compound of the formula I, according to claim 2, wherein $R^3$ and $R^4$ independently of one another represent a hydrogen atom or a methyl or ethyl group or $R^3$ and $R^4$ together represent a 2- to 5-membered alkylene bridge, or a tautomer or pharmaceutically acceptable salt thereof.

6. A compound of the formula I, according to claim 3, wherein $R^3$ and $R^4$ independently of one another represent a hydrogen atom or a methyl or ethyl group or $R^3$ and $R^4$ together represent a 2- to 5-membered alkylene bridge, or a tautomer or pharmaceutically acceptable salt thereof.

7. A compound of the formula I, according to claim 1 wherein, $R^5$, $R^6$ and $R^7$ independently of one another represent hydrogen, optionally substituted $C_1$-$C_{10}$-alkyl, halogen, CN, —$NR^8CO$—($C_1$-$C_5$-alkyl), —$NR^8SO_2$—($C_1$-$C_5$-alkyl), —$CO_2R^8$, —$SO_2R^8$, —$CONHR^8$, —$SO_2NHR^8$ or —$OR^8$ and $R^8$ denotes a hydrogen atom or a $C_1$-$C_5$-alkyl group, or a tautomer or pharmaceutically acceptable salt thereof.

8. A compound of the formula I, according to claim 2, wherein, $R^5$, $R^6$ and $R^7$ independently of one another represent hydrogen, optionally substituted $C_1$-$C_{10}$-alkyl, halogen, CN, —$NR^8CO$—($C_1$-$C_5$-alkyl), —$NR^8SO_2$—($C_1$-$C_5$-alkyl), —$CO_2R^8$, —$SO_2R^8$, —$CONHR^8$, —$SO_2NHR^8$ or —$OR^8$ and $R^8$ denotes a hydrogen atom or a $C_1$-$C_5$-alkyl group, or a tautomer or pharmaceutically acceptable salt thereof.

9. A compound of the formula I, according to claim 3, wherein, $R^5$, $R^6$ and $R^7$ independently of one another represent hydrogen, optionally substituted $C_1$-$C_{10}$-alkyl, halogen, CN, —$NR^8CO$—($C_1$-$C_5$-alkyl), —$NR^8SO_2$—($C_1$-$C_5$-alkyl), —$CO_2R^8$, —$SO_2R^8$, —$CONHR^8$, —$SO_2NHR^8$ or —$OR^8$ and $R^8$ denotes a hydrogen atom or a $C_1$-$C_5$-alkyl group, or a tautomer or pharmaceutically acceptable salt thereof.

10. A compound of the formula I, according to claim 4, wherein, $R^5$, $R^6$ and $R^7$ independently of one another represent hydrogen, optionally substituted $C_1$-$C_{10}$-alkyl, halogen, CN, —$NR^8CO$—($C_1$-$C_5$-alkyl), —$NR^8SO_2$—($C_1$-$C_5$-alkyl), —$CO_2R^8$, —$SO_2R^8$, —$CONHR^8$, —$SO_2NHR^8$ or —$OR^8$ and $R^8$ denotes a hydrogen atom or a $C_1$-$C_5$-alkyl group, or a tautomer or pharmaceutically acceptable salt thereof.

11. A compound of the formula I, according to claim 1, wherein, $R^1$ denotes a phenyl group optionally substituted by a halogen atom or a cyano or nitro group, $R^2$ is optionally substituted by one or more groups $R^{10}$, $R^3$ and $R^4$ independently of one another each denote a methyl or ethyl group or $R^3$ and $R^4$ together represent an ethylene bridge, $R^5$, $R^6$ and $R^7$ independently of one another each denote a hydrogen, fluorine or chlorine atom or a cyano, methoxy, methanesulphonylamino, methanesulphonyl, difluoromethoxy, trifluoromethoxy, difluoromethyl or trifluoromethyl group, $R^9$ denotes a hydrogen atom or an optionally substituted aryl or optionally substituted heteroaryl group, or a tautomer or pharmaceutically acceptable salt thereof.

12. A compound of the formula (I) according to claim 1, wherein $R^1$ denotes a phenyl group optionally substituted by a fluorine, chlorine, bromine or iodine atom or a cyano or nitro group, $R^2$ denotes a group selected from among the optionally substituted groups of general formulae (i)-(vi):

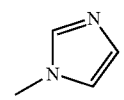

(i)

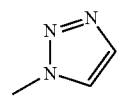

(ii)

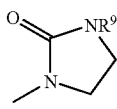

(iii)

-continued (iv)

(v)

(vi)

where $R^9$ denotes a phenyl or pyridyl group optionally substituted by a fluorine atom or by an amino, nitro, hydroxy or methoxy group and the above-mentioned groups (i) to (vi) may each be substituted by one or two groups $R^{10}$ and $R^{10}$ denotes OH, $NO_2$, CN, —$OCHF_2$, —$OCF_3$, —$NH_2$, —NH-alkyl, —N(alkyl)-alkyl, —NH-aryl, —N(alkyl)-aryl, —NHCO-alkyl, —$NHCO_2$-alkyl, —NHCO-aryl, —N(-alkyl)-CO-alkyl, —N(-alkyl)-CO-aryl, —$NHSO_2$-alkyl, —$NHSO_2$-aryl, —N(-alkyl)-$SO_2$-alkyl, —N(-alkyl)-$SO_2$-aryl, —$CO_2$-alkyl, —$SO_2$-alkyl, —$SO_2$-aryl, —CONH-alkyl, —CONH-aryl, —CON(alkyl)-alkyl, —CON(-alkyl)-aryl, —$SO_2$NH-alkyl, —$SO_2$NH-aryl, —$SO_2$N(-alkyl)-alkyl, —$SO_2$N(-alkyl)-aryl, —O-aryl, —S-alkyl, —S-aryl, halogen, $C_1$-$C_{10}$-alkyl, —O—($C_1$-$C_3$-alkyl), —COOH, —$CONH_2$, —CON(-alkyl)-$SO_2$-alkyl, —$CONHSO_2$-alkyl, —CONHOH, 2,5-dihydro-5-oxo-4H-1,2,4-oxadiazol-3-yl, 2,5-dihydro-5-oxo-4H-1,2,4-thiadiazol-3-yl, 2,5-dihydro-2-oxo-3H-1,2,4,5-oxathiadiazol-4-yl, 1-acetyl-2-amino-propen-1-yl, tetrazolyl, heterocyclyl, aryl or heteroaryl, $R^3$ and $R^4$ independently of one another denote a methyl or ethyl group or $R^3$ and $R^4$ together represent an ethylene bridge and $R^5$, $R^6$ and $R^7$ represent a hydrogen, fluorine or chlorine atom or a cyano, methoxy, methanesulphonylamino, methanesulphonyl, difluoromethoxy, trifluoromethoxy, difluoromethyl or trifluoromethyl group, or a tautomer or pharmaceutically acceptable salt thereof.

13. A compound of the formula (I) according to claim 12, wherein $R^1$ denotes a phenyl group optionally substituted by a fluorine, chlorine, bromine or iodine atom or by a cyano or nitro group, $R^2$ denotes a group selected from among the groups of formulae (i)-(vi):

(i)

(ii)

(iii)

(iv)

(v)

(vi)

where $R^9$ denotes a phenyl or pyridyl group optionally substituted by a fluorine atom or by an amino, nitro, hydroxy or methoxy group, and the above-mentioned groups (i) to (vi) may each be substituted by one or two groups $R^{10}$ and $R^{10}$ denotes OH, —$NO_2$, —CN, —$NH_2$, —I, —$N(CH_3)_2$, —$NHCO_2CH_3$, —$NHSO_2CH_3$, $C_1$-$C_3$-alkyl, —$SO_2N(CH_3)_2$, —$CO_2H$, benzyloxycarbonyl, ethoxycarbonyl, methoxycarbonyl, —CONHOH, tetrazol-5-yl, pyridinyl, methoxy-pyridinyl, phenyl optionally substituted by hydroxy, fluorine, methoxy, amino, nitro, dimethylamino, methylcarbonylamino, methylsulphonylamino, dimethylamino-sulphonylamino, carboxy, ethoxycarbonyl, benzyloxycarbonyl, hydroxyaminocarbonyl or tetrazol-5-yl, or thiophenyl, 5-methyl-thiophen-2-yl, 3,5-dimethyl-isoxazol-4-yl or 1-acetyl-2-amino-propenyl, $R^3$ and $R^4$ each denote a methyl or ethyl group or $R^3$ and $R^4$ together represent an ethylene bridge and $R^5$, $R^6$ and $R^7$ each denote a hydrogen atom, or a tautomer or pharmaceutically acceptable salt thereof.

14. A compound of the formula (I) according to claim 13, wherein
R¹ denotes a phenyl group,
R² denotes a group selected from among the groups of formulae (i)-(iii) or (v):

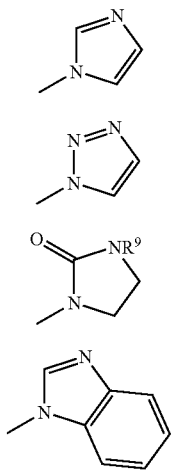

where R⁹ denotes a phenyl or pyridyl group optionally substituted by a fluorine atom or by an amino, nitro, hydroxy or methoxy group,
and the above-mentioned groups (i) to (iii) and (v) may each be substituted by a group R¹⁰ and
R¹⁰ denotes an iodine atom or a nitro, amino, methyl, carboxy, methoxycarbonyl, ethoxycarbonyl, pyridin-4-yl, pyridin-2-yl, 6-methoxy-pyridin-3-yl, thiophen-2-yl, 5-methyl-thiophen-2-yl, 3,5-dimethyl-isoxazol-4-yl, 1-acetyl-2-amino-propen-1-yl or a phenyl group, while the phenyl group may be substituted by a fluorine atom or by a hydroxy, methoxy, nitro, amino, dimethylamino, methylcarbonylamino, methylsulphonylamino, dimethylamino-sulphonylamino, carboxy, ethoxycarbonyl, benzyloxycarbonyl, hydroxyaminocarbonyl or tetrazol-5-yl group,
R³ and R⁴ each denote a methyl group and
R⁵, R⁶ and R⁷ each denote a hydrogen atom,
or a tautomer or pharmaceutically acceptable salt thereof.
15. A compound of the formula (I) according to claim 14, wherein
R¹ denotes a phenyl group,
R² denotes a group of formulae (ia) or (v):

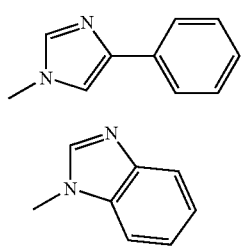

while the above-mentioned group (ia) may be substituted in the phenyl moiety by a fluorine atom or by a hydroxy, methoxy, nitro, amino, dimethylamino, methylcarbonyl-amino, methylsulphonylamino, dim-ethylamino-sulphonylamino, carboxy, ethoxy-carbonyl, benzyloxycarbonyl, hydroxyaminocarbonyl or tetrazol-5-yl group and
the above-mentioned group (v) may be substituted in the benzyl moiety by a nitro, amino, carboxy or C₁₋₂-alkyloxy-carbonyl group,
R³ and R⁴ each denote a methyl group and
R⁵, R⁶ and R⁷ each denote a hydrogen atom,
or a tautomer or pharmaceutically acceptable salt thereof.
16. A compound selected from the group consisting of:
N-(3-{2-[1,1-dimethyl-3-(4-phenyl-imidazol-1-yl)-propylamino]-1-hydroxy-ethyl}-phenyl)-benzenesulphonamide,
N-(3-{2-[1,1-dimethyl-3-(3-methyl-1,4-dioxo-3,4-dihydro-1H-phthalazin-2-yl)-propylamino]-1-hydroxy-ethyl}-phenyl)-benzenesulphonamide,
N-(3-{2-[1,1-dimethyl-3-(2-oxo-3-phenyl-imidazolidin-1-yl)-propylamino]-1-hydroxy-ethyl}-phenyl)-benzenesulphonamide,
N-[3-(2-{1,1-dimethyl-3-[4-(4-nitro-phenyl)-imidazol-1-yl]-propylamino}-1-hydroxy-ethyl)-phenyl]-benzenesulphonamide,
N-[3-(2-{3-[3-(4-fluoro-phenyl)-2-oxo-imidazolidin-1-yl]-1,1-dimethyl-propylamino}-1-hydroxy-ethyl)-phenyl]-benzenesulphonamide,
N-[3-(1-hydroxy-2-{3-[4-(4-methoxy-phenyl)-imidazol-1-yl]-1,1-dimethyl-propylamino}-ethyl)-phenyl]-benzenesulphonamide,
N-[3-(1-hydroxy-2-{3-[4-(4-hydroxy-phenyl)-imidazol-1-yl]-1,1-dimethyl-propylamino}-ethyl)-phenyl]-benzenesulphonamide,
N-[3-(2-{3-[4-(4-amino-phenyl)-imidazol-1-yl]-1,1-dimethyl-propylamino}-1-hydroxy-ethyl)-phenyl]-benzenesulphonamide,
N-[3-(1-hydroxy-2-{3-[4-(4-methanesulphonylamino-phenyl)-imidazol-1-yl]-1,1-dimethyl-propylamino}-ethyl)-phenyl]-benzenesulphonamide,
N-(3-{1-hydroxy-2-[3-(4-iodo-imidazol-1-yl)-1,1-dimethyl-propylamino]-ethyl}-phenyl)-benzenesulphonamide,
methyl 1-{3-[2-(3-benzenesulphonylamino-phenyl)-2-hydroxy-ethylamino]-3-methyl-butyl}-1H-imidazole-4-carboxylate,
N-[3-(1-hydroxy-2-{3-[4-(4-N,N-dimethyl-sulphamoy-lamino-phenyl)-imidazol-1-yl]-1,1-dimethyl-propylamino}-ethyl)-phenyl]-benzenesulphonamide,
N-(3-{2-[1,1-dimethyl-3-(2-oxo-3-pyridin-2-yl-imidazolidin-1-yl)-propylamino]-1-hydroxy-ethyl}-phenyl)-benzenesulphonamide,
1-{3-[2-(3-benzenesulphonylamino-phenyl)-2-hydroxy-ethylamino]-3-methyl-butyl}-1H-imidazole-4-carboxylic acid,
N-(3-{2-[1,1-dimethyl-3-(4-pyridin-4-yl-imidazol-1-yl)-propylamino]-1-hydroxy-ethyl}-phenyl)-benzenesulphonamide,
benzyl 4-(1-{3-[2-(3-benzenesulphonylamino-phenyl)-2-hydroxy-ethylamino]-3-methyl-butyl}-1H-imidazol-4-yl)-benzoate,
4-(1-{3-[2-(3-benzenesulphonylamino-phenyl)-2-hydroxy-ethylamino]-3-methyl-butyl}-1H-imidazol-4-yl)-benzoic acid,
N-[3-(1-hydroxy-2-{3-[3-(4-hydroxy-phenyl)-2-oxo-imidazolidin-1-yl]-1,1-dimethyl-propylamino}-ethyl)-phenyl]-benzenesulphonamide,
N-[4-(1-{3-[2-(3-benzenesulphonylamino-phenyl)-2-hydroxy-ethylamino]-3-methyl-butyl}-1H-imidazol-4-yl)-phenyl]-acetamide, N-[3-(2-{3-[4-(3,5-dimethyl-isoxazol-4-yl)-imidazol-1-yl]-1,1-dimethyl-propylamino}-1-hydroxy-ethyl)-phenyl]-benzenesulphonamide, N-[3-(1-hydroxy-2-{3-[4-(6-methoxy-pyridin-3-yl)-imidazol-1-yl]-1,1-dimethyl-propylamino}-ethyl)-phenyl]-benzenesulphonamide, N-[3-(2-{1,1-dimethyl-3-[4-(5-methyl-thiophen-2-yl)-imidazol-1-yl]-propylamino}-1-hydroxy-ethyl)-phenyl]-benzenesulphonamide, N-[3-(2-{3-[4-(4-fluoro-phenyl)-imidazol-1-yl]-1,1-dimethyl-propylamino}-1-hydroxy-ethyl)-phenyl]-benzenesulphonamide, N-(3-{2-[1,1-dimethyl-3-(5-nitro-benzoimidazol-1-yl)-propylamino]-1-hydroxy-ethyl}-phenyl)-benzenesulphonamide, N-[3-(1-hydroxy-2-{3-[4-(4-methoxy-phenyl)-[1.2.3]triazol-1-yl]-1,1-dimethyl-propylamino}-ethyl)-phenyl]-benzenesulphonamide, N-(3-{2-[1,1-dimethyl-3-(4-thiophen-2-yl-imidazol-1-yl)-propylamino]-1-hydroxy-ethyl}-phenyl)-benzenesulphonamide, N-[3-(2-{3-[4-(4-dimethylamino-phenyl)-imidazol-1-yl]-1,1-dimethyl-propylamino}-1-hydroxy-ethyl)-phenyl]-benzenesulphonamide, ethyl 4-(1-{3-[2-(3-benzenesulphonylamino-phenyl)-2-hydroxy-ethylamino]-3-methyl-butyl}-1H-imidazol-4-yl)-benzoate, N-[3-(1-hydroxy-2-{3-[3-(4-methoxy-phenyl)-2-oxo-imidazolidin-1-yl]-1,1-dimethyl-propylamino}-ethyl)-phenyl]-benzenesulphonamide, N-[3-(2-{1,1-dimethyl-3-[3-(4-nitro-phenyl)-2-oxo-imidazolidin-1-yl]-propylamino}-1-hydroxy-ethyl)-phenyl]-benzenesulphonamide, N-[3-(1-hydroxy-2-{3-[3-(4-methoxy-phenyl)-5-methyl-[1,2,4]triazol-1-yl]-1,1-dimethyl-propylamino}-ethyl)-phenyl]-benzenesulphonamide, N-[3-(2-{3-[3-(4-amino-phenyl)-2-oxo-imidazolidin-1-yl]-1,1-dimethyl-propylamino}-1-hydroxy-ethyl)-phenyl]-benzenesulphonamide, N-[3-(2-{3-[4-(1-acetyl-2-amino-propenyl)-imidazol-1-yl]-1,1-dimethyl-propylamino}-1-hydroxy-ethyl)-phenyl]-benzenesulphonamide, N-(3-{2-[3-(5-amino-benzoimidazol-1-yl)-1,1-dimethyl-propylamino]-1-hydroxy-ethyl}-phenyl)-benzenesulphonamide, 1-{3-[2-(3-benzenesulphonylamino-phenyl)-2-hydroxy-ethylamino]-3-methyl-butyl}-1H-benzoimidazole-5-carboxylic acid, ethyl 1-{3-[2-(3-benzenesulphonylamino-phenyl)-2-hydroxy-ethylamino]-3-methyl-butyl}-1H-benzoimidazole-5-carboxylate, N-{3-[2-(1,1-dimethyl-3-{4-[4-(1H-tetrazol-5-yl)-phenyl]-imidazol-1-yl}-propylamino)-1-hydroxy-ethyl]-phenyl}-benzenesulphonamide, and 4-(1-{3-[2-(3-benzenesulphonylamino-phenyl)-2-hydroxy-ethylamino]-3-methyl-butyl}-1H-imidazol-4-yl)-N-hydroxy-benzamide, or a pharmaceutically acceptable salt thereof.

17. The (R)-enantiomer of a compound according to claim 1, 2, 3, 4, 5, 6, 7, 8, 9, 10, 11, 12, 13, 14, 15 or 16, or a pharmaceutically acceptable salt thereof.

18. A pharmaceutical composition comprising a compound of the formula I according to claim 1, or a pharmaceutically acceptable salt thereof, together with a pharmaceutically acceptable carrier or excipient.

* * * * *